(12) United States Patent
Schweiger et al.

(10) Patent No.: US 9,206,115 B2
(45) Date of Patent: Dec. 8, 2015

(54) ATGLISTATIN AND PHARMACEUTICAL COMPOSITION COMPRISING THE SAME

(71) Applicants: Technische Universität Graz, Graz (AT); Karl-Franzens-Universität Graz, Graz (AT)

(72) Inventors: Martina Schweiger, Graz (AT); Matthias Romauch, Graz (AT); Robert Zimmermann, Graz (AT); Nicole Mayer, Graz (AT); Rolf Breinbauer, Graz (AT)

(73) Assignees: Technische Universität Graz, Graz (AT); Karl-Franzens-Universität Graz, Graz (AT)

( * ) Notice: Subject to any disclaimer, the term of this patent is extended or adjusted under 35 U.S.C. 154(b) by 0 days.

(21) Appl. No.: 14/162,324

(22) Filed: Jan. 23, 2014

(65) Prior Publication Data
US 2014/0206738 A1   Jul. 24, 2014

Related U.S. Application Data

(63) Continuation of application No. 13/841,530, filed on Mar. 15, 2013, now abandoned.

(60) Provisional application No. 61/755,332, filed on Jan. 22, 2013.

(51) Int. Cl.
C07C 69/94 (2006.01)
C07C 229/52 (2006.01)
(Continued)

(52) U.S. Cl.
CPC .............. *C07C 229/52* (2013.01); *C07C 65/24* (2013.01); *C07C 69/78* (2013.01); *C07C 69/94* (2013.01); *C07D 231/14* (2013.01); *C07D 231/18* (2013.01); *C12Q 1/44* (2013.01)

(58) Field of Classification Search
None
See application file for complete search history.

(56) References Cited

U.S. PATENT DOCUMENTS

| 5,998,424 A | 12/1999 | Galemmo, Jr. et al. |
| 7,683,036 B2 | 3/2010 | Esau et al. |

(Continued)

FOREIGN PATENT DOCUMENTS

| WO | WO 2004/063169 A1 | 7/2004 |
| WO | WO 2007/112754 A2 | 10/2007 |

(Continued)

OTHER PUBLICATIONS

Kitamura et al. Heterogenous Pd/C-catalyzed ligand-free Suzuki-Miyaura coupling reaction using aryl boronic esters. Tetrahedron, 63, 2007, 10596-10602.*

(Continued)

*Primary Examiner* — Anna Pagonakis
(74) *Attorney, Agent, or Firm* — Parker Highlander PLLC

(57) ABSTRACT

A compound of formula (I) as defined herein

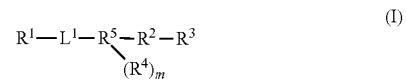

is useful in the treatment and prevention of a disorder such as cachexia, stroke, atherosclerosis, coronary artery disease, and diabetes and pharmaceutical compositions of the same. Also, a method of screening for lipase inhibitors using a compound of formula (I) and determining its lipase inhibitory activity. The method includes in vitro assays of compounds using ATGL and/or HSL, and cellular assays wherein inhibition is followed by observing indicators of efficacy. Also, methods for treatment or prevention of a condition involving cachexia, stroke, artherosclerosis, coronary artery disease, diabetes, preferably diabetes type II by administering a pharmaceutical composition comprising an agent which is able to inhibit ATGL. Also contemplated herein, are compositions comprising one or more ATGL-inhibiting agents optionally in combination with one or more lipase inhibitors or inhibitors of inflammatory cytokines.

2 Claims, 4 Drawing Sheets

(51) Int. Cl.
*C07C 69/78* (2006.01)
*C07D 231/18* (2006.01)
*C07D 231/14* (2006.01)
*C07C 65/24* (2006.01)
*C12Q 1/44* (2006.01)

(56) References Cited

U.S. PATENT DOCUMENTS

| | | |
|---|---|---|
| 2006/0167087 A1 | 7/2006 | Greve et al. |
| 2009/0291906 A1 | 11/2009 | Esau et al. |
| 2010/0004320 A1 | 1/2010 | Elmen et al. |
| 2013/0210883 A1 | 8/2013 | Grillari et al. |

FOREIGN PATENT DOCUMENTS

| | | |
|---|---|---|
| WO | WO 2008/013963 A2 | 1/2008 |
| WO | WO 2010/115825 A2 | 10/2010 |
| WO | WO 2011/072241 A1 | 6/2011 |

OTHER PUBLICATIONS

Walker et al. A rationally designed universal catalyst for Suzuki-Miyaura Coupling Processes. Agnew. Chem. Int. Ed. 2004, 43, 1871-1876.*
International Search Report, Appl. No. PCT/EP2011/058379, Sep. 23, 2011.
Jones et al., "The identification of differently expressed microRNA in osteoarthritic tissue that modulate the production of TNF-α and MMP13," Osteoarthritis and Cartilage, 17(4):464-472 (Apr. 2009).
Sun et al., "Characterization of function and regulation of miR-24-1 and miR-31," Biochemical and Biophysical Research Communications, 380(3):660-665 (Mar. 2009).
Valastyan et al., "A Pleiotropically Acting MicroRNA, miR-31, Inhibits Breast Cancer Metastasis," Cell, 137(6):1032-1046 (Jun. 2009).
International Search Report and Written Opinion, Appl. No. PCT/EP2014/051153, Mar. 21, 2014.
Carini et al., "Nonpeptide Angiotensin II Receptor Antagonists: N-[(Benzyloxy)benzyl]imidazoles and Related Compounds as Potent Antihypertensives," J. Med. Chem., 1990, 33:1330-1336.
Chodorowski-Kimmes et al., "Synthesis of Bridging Electron Transfer Donor Ligands," Tetrahedron Letters, 1997, 38(21):3659-3662.
Dressen et al., "Preparation and Optimization of a Series of 3-Carboxamido-5-phenacylaminopyrazole Bradykinin B1 Receptor Antagonists," J. Med. Chem., 2007, 50:5161-5167.
Grovenstein, Jr. et al., "Carbanions. 21. Reactions of 2- and 3-p-Biphenylylalkyl Chlorides with Alkali Metals. Preparation of Labile Spiro Anions," J. Org. Chem., 1982, 47:2928-2939.
Kern et al., "Synthese von Makromolekeln einheitlicher Größe. II. Mitt. Synthese neuer Diol-oligo-urethane nach dem Duplikationsverfahren," (Synthesis of macromolecules. II. Synthesis of new diol oligourethans), Macromolecular Chemistry and Physics, 1955, 16:89-107.
Kitamura et al., "Heterogeneous Pd/C-catalyzed ligand-free Suzuki Miyaura coupling reaction using aryl boronic esters," Tetrahedron, 2007, 63:10596-10602.
Mamalis et al., "142. Some Heterocyclic N-Oxides," Journal of the Chemical Society, 1950, Part I, pp. 703-711.
Mayer et al., "Development of small-molecule inhibitors targeting adipose triglyceride lipase," Nature Chemical Biology, Oct. 2013, 9(12):785-787.
Seki et al., "Studies on Hypolipidemic Agents. II. Synthesis and Pharmacological Properties of Alkylpyrazole Derivatives," Chem. Pharm. Bull.,1984, 32(4):1568-1577.
Walker et al., "Coupling Catalyst. A Rationally Designed Universal Catalyst for Suzuki-Miyaura Coupling Processes," Angew. Chem. Im. Ed., 2004, 43:1871-1876.

* cited by examiner (A)

| 1 | 2 | 3 | 4 |
|---|---|---|---|
| IC$_{50}$ (µM): 50 +/- 10 | 40 +/- 8 | 12 +/- 3 | 0.7 +/- 0.1 |

(B)

(C)

SEQUENCE LISTING

```
<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: ATGL Forward Primer

<400> SEQUENCE: 1
tggtaccgtt cccgagggag accaagtgga                                  30

<210> SEQ ID NO 2
<211> LENGTH: 27
<212> TYPE: DNA
<213> ORGANISM: Artificial Sequence
<220> FEATURE:
<223> OTHER INFORMATION: ATGL Reverse Primer

<400> SEQUENCE: 2
cctcgagcgc aaggcgggag gccaggt                                     27

<210> SEQ ID NO 3
<211> LENGTH: 31
<212> TYPE: DNA
<213> ORGANISM: Artificial Sequence
<220> FEATURE:
<223> OTHER INFORMATION: HSL Forward Primer

<400> SEQUENCE: 3
tggtacctat ggatttacgc acgatgacac a                                31

<210> SEQ ID NO 4
<211> LENGTH: 28
<212> TYPE: DNA
<213> ORGANISM: Artificial Sequence
<220> FEATURE:
<223> OTHER INFORMATION: HSL Reverse Primer

<400> SEQUENCE: 4
cctcgagcgt tcagtggtgc agcaggcg                                    28

<210> SEQ ID NO 5
<211> LENGTH: 20
<212> TYPE: DNA
<213> ORGANISM: Artificial Sequence
<220> FEATURE:
<223> OTHER INFORMATION: PCR Forward Primer

<400> SEQUENCE: 5
tggaacatct cattcgctgg                                             20

<210> SEQ ID NO 6
<211> LENGTH: 19
<212> TYPE: DNA
<213> ORGANISM: Artificial Sequence
<220> FEATURE:
<223> OTHER INFORMATION: PCR Reverse Primer

<400> SEQUENCE: 6
aatgccgcca tccacatag                                              19
```

ATGLISTATIN AND PHARMACEUTICAL COMPOSITION COMPRISING THE SAME

CROSS-REFERENCE TO RELATED APPLICATIONS

This application is a continuation of U.S. application Ser. No. 13/841,530 filed Mar. 15, 2013 which claims the benefit of U.S. application no. 61/755,332 filed Jan. 22, 2013.

FIELD OF THE INVENTION

The present invention relates to lipase inhibitors, methods of screening therefor, and to methods of prevention, treatment or alleviation of a disorder that can be influenced by lowering lipase activity.

BACKGROUND OF THE INVENTION

In mammals, triglycerides are stored in adipose tissue providing the primary source of energy during periods of food deprivation. Whole body energy homeostasis depends on the precisely regulated balance of lipid storage and mobilization. White adipose tissue (WAT) functions as buffer for dietary lipids and stores excess energy in the form of triacylglycerol (TG). Mobilization of fatty acids from TG stores in adipose tissue critically depends on the activation of lipolytic enzymes. Upon demand, TG stores are hydrolyzed by lipolytic enzymes and the body is provided with free fatty acids (FA) for energy conversion or for the synthesis of complex lipids. Efficient lipolysis requires a three-step process involving three enzymes: Adipose triglyceride lipase (ATGL, also annotated as patatin-like phospholipase domain containing 2, desnutrin, phospholipase A2zeta, and transport secretion protein 2.2), hormone-sensitive lipase (HSL), and monoglyceride lipase (MGL). ATGL removes the first fatty acid from the TG molecule and generates diacylglycerol (DG). HSL is the rate-limiting enzyme for the hydrolysis of DG and MGL performs the last step in this reaction leading to the liberation of FA and glycerol.

FA mobilization in WAT and non-adipose tissues is strongly dependent on ATGL and its co-activator protein CGI-58 (comparative gene expression 58, also known as α/β hydrolase fold-containing 5). In humans, loss-of-function mutations in either of these genes are associated with Neutral Lipid Storage Disease (NLSD), a rare autosomal recessive disorders characterized by the excessive accumulation of neutral lipids in multiple tissues. Similarly as observed in humans, a complete absence of ATGL function in mice is associated with severely reduced lipolysis, obesity, and fat deposition in virtually all tissues of the body. Under fasting conditions, ATGL-deficient animals are unable to mobilize sufficient energy in the form of FA to maintain normal energy homeostasis. Prolonged starvation induces a torpor-like metabolic state characterized by decreased plasma FA concentrations, hypoglycemia, reduced oxygen consumption, and hypothermia. It has been observed that increased circulating FA concentrations, as seen in obesity, can promote fat deposition, insulin resistance, and inflammation in non-adipose tissues. These adverse effects of ectopic lipid overload are known under the term "lipotoxicity" and central in the pathogenesis of metabolic disorders.

Dysfunctional lipolysis affects energy homeostasis and may contribute to the pathogenesis of obesity and insulin resistance. Dysregulation of TG-lipolysis in man has been linked to variations in the concentration of circulating FA, an established risk factor for the development of insulin resistance (Bergman, R. N. et al (2001) J Investig Med 49: 119-26; Blaak, E. E. (2003) Proc Nutr Soc 62: 753-60; Boden, G. and G. I. Shulman (2002) Eur J Clin Invest 32(Suppl 3):14-23; Arner, P. (2002) Diabetes Metab Res Rev 18(Suppl 2): S5-9).

During periods of increased energy demand, lipolysis in adipocytes is activated by hormones, such as catecholamines. Hormone interaction with G-protein coupled receptors is followed by increased adenylate cyclase activity, increased cAMP levels, and the activation of cAMP-dependent protein kinase (protein kinase A, PKA) (Collins, S. and R. S. Surwit (2001) Recent Prog Horm Res 56:309-28). PKA then phosphorylates targets with established function in lipolysis including hormone-sensitive lipase (HSL), resulting in the translocation of HSL from the cytoplasm to the lipid droplet where efficient TG hydrolysis occurs (Sztalryd, C. et al (2003) J Cell Biol 161:1093-103).

The mobilization of free fatty acids from adipose triacylglycerol (TG) stores requires the activities of triacylglycerol hydrolases. Adipose triglyceride lipase (ATGL) and hormone-sensitive lipase (HSL) are the major enzymes contributing to TG breakdown. ATGL (also named PNPLA 2 (patatin-like phospholipase domain containing protein-2, desnutrin, phospholipase A2δ, and transport-secretion protein)) is highly expressed in adipose tissue and specifically removes the first fatty acid from the TG molecule, generating FFA and DG (Zimmermann, R. et al (2004) Science 306: 1383-1386; Wang, S P et al (2001) Obes Res 9:119-128; Villena, J A et al (2004) J Biol Chem 279:47066-47075; Jenkins, C M et al (2004) J Biol Chem 279:48968-48975). An essential role of ATGL in lipolypsis has been demonstrated in studies of ATGL-deficient (ATGL-ko) mice (Haemmerle, G. et al (2006) Science 312:734-737). ATGL-deficient mice accumulated large amounts of lipid in the heart, causing cardiac dysfunction and premature death. The relative contribution of these hydrolases to the lipolytic catabolism of fat has been determined, in mutant mouse models lacking ATGL or HSL (Schweiger, M. et al (2006) J Biol Chem 281(52): 40236-40241). Both HSL and ATGL enzymes contribute to hydrolysis of TG, however, ATGL deficient mice studies indicate that ATGL is rate limiting in the catabolism of cellular fat deposits and plays an important role in energy homeostasis (Haemmerle, G. et al (2006) Science 312(5774):734-737).

Cachexia is a life-threatening syndrome characterized by the unattended loss of body weight, muscle atrophy, fatigue, weakness and significant loss of appetite in someone who is not actively trying to lose weight. It can be a sign of various underlying disorders. It occurs in about 50% of cancer patients but is also observed in other diseases including certain infectious diseases (e.g. tuberculosis, AIDS), in or alcoholchronic obstructive pulmonary disease, and advanced organ failure (liver, heart, kidney). Cachexia physically weakens patients to a state of immobility stemming from loss of appetite, asthenia, and anemia, and response to standard treatment is usually poor (Lainscak M, et al (2007) Curr Opin Support Palliat Care 1(4): 299-305; Bossola M et al (2007) Expert Opin Investig Drugs 16 (8): 1241-53). Recently, is has been shown that lipolysis is also increased in cancer associated cachexia, leading to a loss of adipose tissue (Thompson et al). Another study provided evidence that ATGL deficiency protects from cancer cachexia associated loss of adipose tissue and skeletal muscle (Das, 2011). Thus, inhibiting ATGL might provide a novel medical intervention technique to prevent the loss of adipose and skeletal muscle mass in cancer cachexia. This could prevent uncontrolled weight loss and increase life expectancy of cancer patients.

Cachexia is also prevalent in HIV patients before the advent of highly active anti-retroviral therapy (HAART) and in patients that have any of the range of illnesses classified as "COPD" (chronic obstructive pulmonary disease), particularly emphysema. Some severe cases of schizophrenia can present this condition where it is named vesanic cachexia (from vesania, a Latin term for insanity). Metabolic syndrome is a name for a group of risk factors that occur together and increase the risk for coronary artery disease, stroke, and type 2 diabetes. All of the risks for the syndrome are related to obesity. The two most important risk factors for metabolic syndrome are: Extra weight around the middle and upper parts of the body (central obesity), and insulin resistance. As a result, blood glucose and fat levels rise. Other risk factors include lack of exercise and age. Metabolic syndrome is associated with dyslipidemia and especially increased plasma levels of FA may have a causal role in the development of the syndrome.

Moreover, increased blood levels of FA are also a risk factor for the development of atherosclerosis, stroke, and coronary artery disease. To prevent or treat disorders caused by dyslipidemia, an effective tool represents may be the effective reduction of excessive blood FA levels.

SUMMARY OF THE INVENTION

The invention provides a compound of formula (I) as defined herein

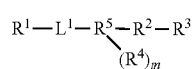

that is useful in the treatment and prevention of a disorder. The disorder comprises cachexia, stroke, atherosclerosis, coronary artery disease, diabetes and disorders and conditions associated therewith. The invention also provides a method of screening for lipase inhibitors using a compound of formula (I) and determining its lipase inhibitory activity.

Aspects of the present method include the in vitro assay of compounds using ATGL and/or HSL, and cellular assays wherein inhibition is followed by observing indicators of efficacy, including alteration of the release of free fatty acid, TG hydrolysis, binding affinity, lowering blood FFA values etc. Another aspect of the invention is a method of treatment or prevention of a condition involving cachexia, stroke, artherosclerosis, coronary artery disease, diabetes, preferably diabetes type II, and its associated or related disorders and conditions, including weight loss, muscle atrophy or wasting, in a subject suffering or susceptible thereto, by administering a pharmaceutical composition comprising an agent which is able to inhibit ATGL. Also contemplated herein, are compositions comprising one or more ATGL-inhibiting agents of the invention, alone, or in combination with each other or in combinations with one or more lipase inhibitors, such as HSL or MGL inhibitors, and/or inhibitors of inflammatory cytokines such as tumor necrosis factor-alpha (TNF-α), interleukins 1 and 6 (IL-1 and IL-6), interferon gamma (IFN-γ), and leukemia-inhibitory factor (LAF).

BRIEF DESCRIPTION OF THE FIGURES

Other features and advantages of the invention will become apparent from a consideration of the ensuing description taken in conjunction with the following illustrative drawings, wherein:

Referring to FIGS. 1B and 1C, for the determination of lipase activity, lysates of E. coli overexpressing recombinant strep-tagged ATGL and CGI-58 were incubated with a substrate containing radiolabeled [9,10-3H(N)]-triolein. Subsequently, FA were extracted and quantified by liquid scintillation counting. Lysates of cells expressing empty vector were set as blank. Inhibitors were solubilized in DMSO and added at the indicated concentrations. DMSO alone was used as negative control. (A) Structure and IC50 values of compound 1-4. (B) Dose-dependent inhibition of ATGL in the presence of compound 3 and 4. The insert in (B) shows a Western blot confirming the expression of Strep-tagged proteins at their correct molecular weight. (C) Lineweaver-Burk plots for kinetic analysis of ATGL inhibition. Experiments were performed at varying concentrations of substrate (0.05-3 mM) in presence and absence of compound 4 (Atglistatin). The insert shows the intersection with the y- and x-axis representing 1/Vmax and -1/Km, respectively. Data are presented as mean+/- S.D. of triplicate determinations. Data for compound 4 are representative for at least three independent experiments.

For FIGS. 2A to 2D, the lipase activity of ATGL, HSL, lipoprotein lipase, and pancreatic lipase was determined using triolein as substrate. MGL activity was detected in the presence of rac-(1,3)-monooleoylglycerol as substrate. Inhibitors were solubilized in DMSO and added at the indicated concentrations. DMSO alone was used as negative control. (A) Dose-dependent inhibition of TG hydrolase activity in WAT lysates obtained from wild-type and ATGL-ko mice. (B) Inhibition of TG hydrolase activity in wild-type WAT lysates by Atglistatin (40 μM) and by the HSL inhibitor Hi 76-0079 (20 μM). (C) Effect of Atglistatin on murine MGL (purified from E. coli), and murine HSL (overexpressed in COS-7 lysates) activity. (D) Effect of Atglistatin on purified bovine LPL (Sigma) and pancreatic lipase (from porcine pancreas, Sigma). Data are presented as mean+/- S.D. of triplicate determinations and are representative for at least three independent experiments (p<0.05 , p<0.01; *, p<0.001).

FIGS. 3A and 3B show differentiated 3T3 cells that were preincubated with the indicated concentrations of Atglistatin. Thereafter, the medium was replaced by DMEM containing 2% BSA (fatty acid free), 10 μM forskolin, in the presence or absence of inhibitors. The release of FA (3A) and glycerol (3B) in the media was determined using commercial kits. Basal FA and glycerol release (not shown) was barely detectable under the applied conditions. Data are presented as mean+/- SD and are representative for 2 independent experiments.

FIGS. 3C to 3F show the effect of Atglistatin on WAT basal (3C, 3D) and forskolin-stimulated (3E, 3F) lipolysis. Adipose tissue pieces (~15 mg, n=5 for each concentration) of wild-type mice were cultured for 8 h in DMEM containing 2% FA-free BSA and the indicated concentrations of Atglistatin. Subsequently, the medium was replaced by identical fresh medium and samples were collected after incubation for another hour in the presence or in the absence of 10 µM forskolin. Atglistatin was solubilized in DMSO and DMSO alone was used as negative control. Data are presented as mean+/− S.D. (*, p<0.05 , p<0.01; *, p<0.001).

Figure 4:
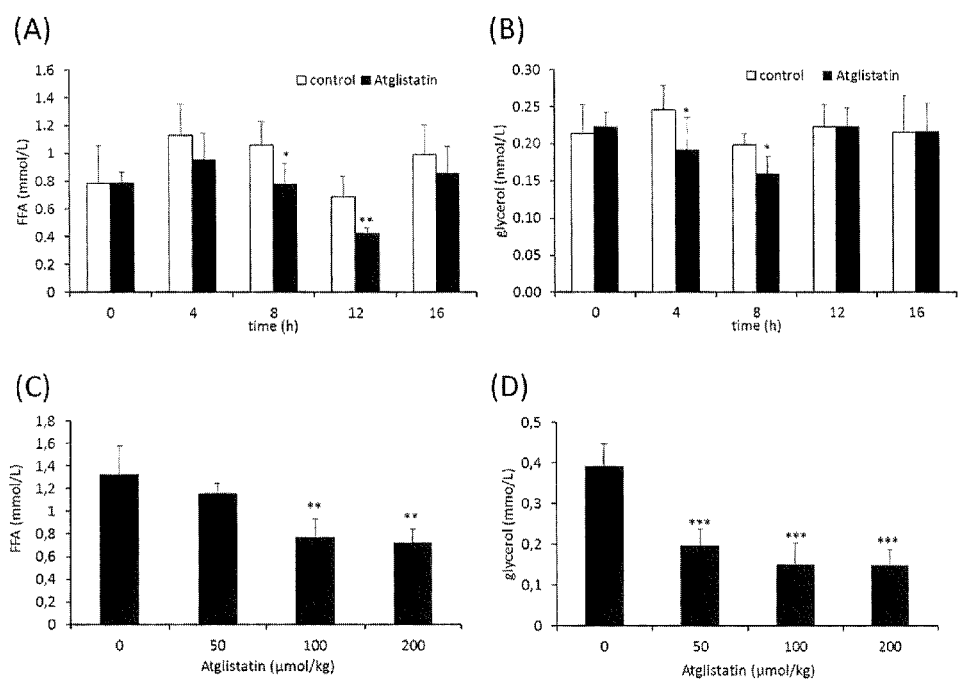
FIGS. 4(A), 4(B), 4(C) and 4(D) are graphs that show the inhibition of lipolysis in vivo.

FIGS. 4A and 4B show the time dependent effect of Atglistatin on plasma free fatty acids (FFA) and glycerol levels of mice. C57Bl6 mice were fasted overnight (ON) and received an oral gavage containing 100 µmol/kg Atglistatin dissolved in olive oil, or olive oil as control. At the indicated timepoints blood was taken retroorbitally and plasma parameters were measured using commercial kits.

FIGS. 4C and 4D show the dose dependent effect of Atglistatin on plasma FFA and glycerol levels of mice. C57Bl6 mice were fasted ON and received an oral gavage containing 0, 50, 100, or 200 µmol/kg Atglistatin dissolved in olive oil, or olive oil as control. 8 h after gavage blood was taken retroorbitally and plasma parameters were measured using commercial kits. Data are presented as mean+S.D. (*, p<0.05 , p<0.01; *, p<0.001). n=5.

DETAILED DESCRIPTION OF THE INVENTION

The following terms are intended to have the meanings presented therewith below and are useful in understanding the description and intended scope of the present invention.

The term 'agent' means any molecule, including polypeptides, antibodies, polynucleotides, chemical compounds and small molecules. In particular the term agent includes compounds such as test compounds or drug candidate compounds.

The term 'agonist' refers to a ligand that stimulates the receptor the ligand binds to in the broadest sense.

As used herein, the term 'antagonist' is used to describe a compound that does not provoke a biological response itself upon binding to a receptor, but blocks or dampens agonist-mediated responses, or prevents or reduces agonist binding and, thereby, agonist-mediated responses.

The term 'assay' means any process used to measure a specific property of an agent. A 'screening assay' means a process used to characterize or select agents based upon their activity from a collection of agents.

The term 'binding affinity' is a property that describes how strongly two or more compounds associate with each other in a non-covalent relationship. Binding affinities can be characterized qualitatively (such as 'strong', 'weak', 'high', or 'low') or quantitatively (such as measuring the $K_D$).

The term 'carrier' means a non-toxic material used in the formulation of pharmaceutical compositions to provide a medium, bulk and/or useable form to a pharmaceutical composition. A carrier may comprise one or more of such materials such as an excipient, stabilizer, or an aqueous pH buffered solution. Examples of physiologically acceptable carriers include aqueous or solid buffer ingredients including phosphate, citrate, and other inorganic and organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

The term 'complex' means the entity created when two or more compounds bind to, contact, or associate with each other.

The term 'compound' is used herein in the context of a 'test compound' or a 'drug candidate compound' described in connection with the assays of the present invention.

As such, these compounds comprise organic or inorganic compounds, derived synthetically, recombinantly, or from natural sources.

The compounds include inorganic or organic compounds such as polynucleotides, lipids, hormone analogs, or other small molecules. Other biopolymeric organic test compounds include peptides comprising from about 2 to about 40 amino acids and larger polypeptides comprising from about 40 to about 500 amino acids, including polypeptide ligands, enzymes, receptors, channels, antibodies or antibody conjugates.

The term 'condition' or 'disease' means the overt presentation of symptoms (i.e., illness) or the manifestation of abnormal clinical indicators (for example, biochemical indicators or diagnostic indicators). Alternatively, the term 'disease' refers to a genetic or environmental risk of or propensity for developing such symptoms or abnormal clinical indicators.

The term 'contact' or 'contacting' means bringing at least two moieties together, whether in an in vitro system or an in vivo system.

The term 'derivatives of a polypeptide' relates to those peptides, oligopeptides, polypeptides, proteins and enzymes that comprise a stretch of contiguous amino acid residues of the polypeptide and that retain a biological activity of the protein, for example, polypeptides that have amino acid mutations compared to the amino acid sequence of a naturally-occurring form of the polypeptide. A derivative may further comprise additional naturally occurring, altered, glycosylated, acylated or non-naturally occurring amino acid residues compared to the amino acid sequence of a naturally occurring form of the polypeptide. It may also contain one or more non-amino acid substituents, or heterologous amino acid substituents, compared to the amino acid sequence of a naturally occurring form of the polypeptide, for example a reporter molecule or other ligand, covalently or non-covalently bound to the amino acid sequence.

The term 'derivatives of a polynucleotide' relates to DNA-molecules, RNA-molecules, and oligonucleotides that comprise a stretch of nucleic acid residues of the polynucleotide, for example, polynucleotides that may have nucleic acid mutations as compared to the nucleic acid sequence of a naturally occurring form of the polynucleotide. A derivative may further comprise nucleic acids with modified backbones such as PNA, polysiloxane, and 2'-O-(2-methoxy) ethyl-phosphorothioate, non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection.

The term 'endogenous' shall mean a material that a mammal naturally produces. Endogenous in reference to the term 'protease', 'kinase', 'factor', or 'receptor' shall mean that which is naturally produced by a mammal (for example, and not limitation, a human). In contrast, the term non-endogenous in this context shall mean that which is not naturally produced by a mammal (for example, and not limitation, a human). Both terms can be utilized to describe both in vivo and in vitro systems. For example, and without limitation, in a screening approach, the endogenous or non-endogenous target (e.g., ATGL and/or HSL, alternative species forms, isoforms, and variants) may be in reference to an in vitro screening system. As a further example and not limitation, where the genome of a mammal has been manipulated to include a non-endogenous target, screening of a candidate compound by means of an in vivo system is viable.

The term 'expressible nucleic acid' means a nucleic acid coding for a proteinaceous molecule, an RNA molecule, or a DNA molecule.

The term 'expression' comprises both endogenous expression and overexpression by transduction.

The term 'expression inhibitory agent' means a polynucleotide designed to interfere selectively with the transcription, translation and/or expression of a specific polypeptide or protein normally expressed within a cell. More particularly, 'expression inhibitory agent' comprises a DNA or RNA molecule that contains a nucleotide sequence identical to or complementary to at least about 15-30, particularly at least 17, sequential nucleotides within the polyribonucleotide sequence coding for a specific polypeptide or protein. Exemplary expression inhibitory molecules include ribozymes, double stranded siRNA molecules, self-complementary single-stranded siRNA molecules (shRNA), genetic antisense constructs, and synthetic RNA antisense molecules with modified stabilized backbones.

The term 'inhibit' or 'inhibiting', in relationship to the term 'response' means that a response is decreased or prevented in the presence of a compound as opposed to in the absence of the compound.

The term 'inhibition' refers to the reduction, down regulation of a process or the elimination of a stimulus for a process, which results in the absence or minimization of the expression or activity of a protein or polypeptide.

The term 'pharmaceutically acceptable salts' refers to the non-toxic, inorganic and organic acid addition salts, and base addition salts, of compounds which inhibit the expression or activity of targets as disclosed herein. These salts can be prepared in situ during the final isolation and purification of compounds useful in the present invention.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The term 'solvate' means a physical association of a compound useful in this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

The term 'subject' includes humans and other mammals. In the context of this invention, it is particularly envisaged that mammals are to be treated which are economically, agronomically or scientifically important. Scientifically important organisms include, but are not limited to, mice, rats, and rabbits. Non-limiting examples of agronomically important animals are sheep, cattle and pigs, while, for example, cats and dogs may be considered as economically important animals. Preferably, the subject is a human.

'Therapeutically effective amount' means that amount of a drug, compound, expression inhibitory agent, or pharmaceutical agent that will elicit the biological or medical response of a subject that is being sought by a medical doctor or other clinician.

The term 'treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, 'treating' or 'treatment' relates to slowing the progression of the disease.

The term "vectors" also relates to plasmids as well as to viral vectors, such as recombinant viruses, or the nucleic acid encoding the recombinant virus.

The term "vertebrate cells" means cells derived from animals having vertera structure, including fish, avian, reptilian, amphibian, marsupial, and mammalian species. Preferred cells are derived from mammalian species, and most preferred cells are human cells. Mammalian cells include feline, canine, bovine, equine, caprine, ovine, porcine murine, such as mice and rats, and rabbits.

Lipolytic activity may be detected by assay methods known to those of skill in the art. Preferably, methods such as described hereinunder in Examples 1 and 7 are used. In a preferred embodiment of the invention, the method as described herein in paragraphs 1-3 of example 7 herein, including references made therein, is used. A preferred embodiment of the invention includes measurement of lipase activity according to Jenkins et al. and Chung et al. as described in Example 7 herein. A further preferred embodiment of the invention includes measurement of lipase activity as described Example 7 using HIS-tagged ATGL. Any such assays and tests are described for the purpose of illustration and guidance; variations, alterations, adaptations and modifications will be obvious and possible to the person of skill in the art. For instance, the test described in example 7 may be used to test the lipolytic activity and if desired the inhibition thereof by a given inhibitor, among others, of variants, fragments, variants due to premature termination or the like, of a lipase, preferably of ATGL lipase, without deviating from the scope of the invention.

The target is the structure used to detect the desired activity of a compound of the invention. It is preferably a lipase, more preferably ATGL, and particularly human ATGL. The amino acid and nucleic acid sequences for ATGL are known to the skilled artisan. For example, the ATGL sequence is set out in FIG. 7 (human ATGL) and FIG. 8 (mouse ATGL) of WO2010115825.

The term "cachexia and its associated or related disorders and conditions" or "cachexia and its related conditions or physiology" or variants thereof, refers to a disease or condition which involves, results at least in part from, or includes loss of weight, muscle atrophy, fatigue, weakness and significant loss of appetite in someone who is not actively trying to lose weight. It can be associated with or result from (directly or indirectly) various underlying disorders including cancer, metabolic acidosis (from decreased protein synthesis and increased protein catabolism), certain infectious diseases (e.g. tuberculosis, AIDS), some autoimmune disorders, addiction to drugs such as amphetamines or cocaine, chronic alcoholism and cirrhosis of the liver, chronic inflammatory disorders, anorexia, and neurodegenerative disease. In a particular aspect, cachexia is cancer cachexia. In other such aspects, muscle wasting and/or unintended body weight loss associated with neurological conditions, immobility or impaired mobility due to various diseases such as neurodegenerative disease, MS, spinal cord injury, is included in the term.

The term "alkyl" relates to a monovalent saturated aliphatic (i.e. non-aromatic) acyclic hydrocarbon group (i.e. a group consisting of carbon atoms and hydrogen atoms) which may be linear or branched and does not comprise any carbon-to-carbon double bond or any carbon-to-carbon triple bond.

The term "alkenyl" refers to a monovalent unsaturated aliphatic acyclic hydrocarbon group which may be linear or branched and comprises at least one carbon-to-carbon double bond while it does not comprise any carbon-to-carbon triple bond.

The term "alkynyl" refers to a monovalent unsaturated aliphatic acyclic hydrocarbon group which may be linear or branched and comprises at least one carbon-to-carbon triple bond and optionally one or more carbon-to-carbon double bonds.

The term "alkylene" refers to an alkanediyl group including straight chain and/or branched chain groups.

The term "alkenylene" refers to an alkenediyl group including straight chain and/or branched chain groups, and comprising at least one carbon-to-carbon double bond, while it does not comprise any carbon-to-carbon triple bond.

The term "alkynylene" refers to an alkynediyl group including straight chain and/or branched chain groups, and comprising at least one carbon-to-carbon triple bond and optionally one or more carbon-to-carbon double bonds.

The term "aryl" refers to a monovalent aromatic hydrocarbon group, including bridged ring and/or fused ring systems, containing at least one aromatic ring. "Aryl" may, for example, refer to phenyl, naphthyl or anthracenyl.

The term "heteroaryl" refers to a monocyclic or fused-ring polycyclic group having 5 to 14 ring atoms, having 6, 10 or 14 pi electrons shared in a cyclic array, and containing carbon ring atoms and 1, 2 or 3 hetero ring atom independently selected from O, N, or S. The term "heteroaryl" may, for example, relate to thiophenyl (thienyl), furanyl (furyl), pyrrolyl, imidazolyl, pyrazolyl, pyridinyl (pyridyl; including, e.g., 2-pyridyl, 3-pyridyl, and 4 pyridyl), pyrazinyl, pyrimidinyl, pyridazinyl, oxazolyl, isoxazolyl, or furazanyl.

The term "heteroaryl having 5 or 6 ring atoms, wherein 1, 2 or 3 ring atoms are each independently selected from oxygen, sulfur, or nitrogen and the other ring atoms are carbon atoms" refers to a monocyclic group having 5 or 6 ring atoms (i.e., ring members), having 6 pi electrons shared in a cyclic array, and containing carbon atoms and 1, 2 or 3 heteroatoms independently selected from O, N, or S. Non-limiting examples of heteroaryl groups include thiophenyl (thienyl), furanyl (furyl), pyrrolyl, imidazolyl, pyrazolyl, pyridinyl (pyridyl; including, e.g., 2-pyridyl, 3-pyridyl, and 4 pyridyl), pyrazinyl, pyrimidinyl, pyridazinyl, oxazolyl, isoxazolyl, and furazanyl.

The term "halogen" refers to fluoro, chloro, bromo, or iodo, and in particular to fluoro, chloro, or bromo.

The present invention provides the first small molecule inhibitor for ATGL having $IC_{50}$ concentrations in the submicromolar range. The inhibitor is preferably a competitive inhibitor and does not affect the activity of other known acylglycerol hydrolases. Further, the inhibitor is preferably orally bioavailable and capable of inhibiting lipolysis in vivo. It is therefore capable of serving as lead structure for the identification of further inhibitors.

FA metabolism is closely linked to the development of metabolic disorders. Increased lipolysis can promote lipid overload of non-adipose tissues such as liver, skeletal and cardiac muscle, and pancreas, which causes lipotoxicity impairing the metabolic functions of these tissues (Boden, 2011). Mice lacking ATGL exhibit improved glucose tolerance and insulin sensitivity and are resistant to high-fat diet-induced insulin resistance implicating that inhibition of ATGL represents a strategy to improve insulin resistance (Haemmerle, 2006; Kienesberger, 2009). Apparently, ATGL-deficiency causes a shift from fatty acid to glucose usage in insulin-sensitive tissues which is opposite to that observed in type 2 diabetes. Notably, ATGL-deficient animals show improved insulin sensitivity despite severe TG accumulation in non-adipose tissues indicating that increased ectopic lipid storage per se does not cause lipotoxicity. In fact, ATGL activity generates FA required for the synthesis of lipotoxic metabolites such as acyl-CoA (Li, 2010), ceramides (Summers, 2006), and diglycerides (Samuel, 2010) which cause insulin resistance.

ATGL deficiency is associated with a severe metabolic phenotype characterized by TG accumulation in multiple tissues which is most pronounced in the heart causing cardiomyopathy and premature death in ATGL-ko mice (Haemmerle, 2006). TG accumulation seems to be the only cause for premature death since ATGL-ko animals overexpressing ATGL exclusively in cardiac muscle exhibit normal life expectancy (Haemmerle, 2011). Similarly, humans with defective ATGL function develop cardiac myopathy which is lethal or necessitates cardiac transplantation (Hirano, 2008). It is reasonable to assume that also inhibitor-mediated ablation of ATGL activity can cause cardiac TG accumulation limiting the potential value of ATGL inhibitor as therapeutic target. However, TG accumulation in the mouse heart is slowly progressive and humans with defective ATGL function reach adulthood. Severe cardiac myopathy appears to develop at ~30 years of age (Hirano, 2009) suggesting that transient inhibition of ATGL must not necessarily result in cardiac dysfunction since tissue TG stores can be rapidly mobilized for energy production or membrane lipid synthesis.

Importantly, the compounds of the present invention do not result in TG accumulation in heart and other tissues in treated mice although lipolytic parameters were significantly reduced. This implicates that a more severe and continuous inhibition of ATGL activity is required for ectopic TG accumulation. Reduced circulating glycerol and FA levels suggest that the compounds of the present invention efficiently inhibits WAT lipolysis. Thus, the compounds of formula (I), preferably compound 4, represent a suitable tool to advance the development of drugs for the treatment of the metabolic syndrome.

Another devastating disease which is strongly linked with deregulated lipolysis is cachexia, a complex metabolic disorder characterized by general physical wasting and frequently associated with cancer (Tisdale, 2010, Ryden, 2008). Cancer-associated cachexia leads to depletion of adipose and muscle tissue mass and is considered as important adverse prognostic factor responsible for the immediate cause of death in an estimated 15% of all cancer patients (Deans, 2005). Importantly, ATGL-deficiency in mice protects from cancer-induced WAT loss. Moreover, these mice are also resistant to muscle loss although the protective mechanism remains unexplained (Das, 2011). In this respect, it is important to note that insulin resistance is present in many cancer patients and may be one mechanism through which muscle wasting occurs (Honors, 2012). Ectopic lipid accumulation induced by muscle-specific overexpression of LPL in mice has been shown to result in increased proteasomal activity, apoptosis and skeletal muscle damage (Tamilarasan, 2012). Similarly, cancer-mediated loss of adipose tissue due to elevated lipolysis could have lipotoxic effects in non-adipose tissues promoting insulin resistance and muscle loss. Thus, pharmacological inhibition of ATGL may also help to prevent cachexia.

In a further aspect of the invention, the compounds of the invention are provided as tool compounds to study the pathophysiology of FA metabolism and offer new opportunities to understand the chemical biology of ATGL.

In one aspect, the invention relates to a compound of formula (I),

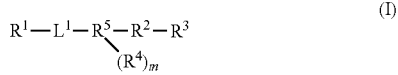

(I)

wherein R1-R5, L1, m have the meanings defined herein, or a pharmaceutically acceptable salt, solvate or prodrug thereof.

In particular:

$L^1$ is a bond, $C_{1-10}$ alkylene, $C_{2-10}$ alkenylene, or $C_{2-10}$ alkynylene, wherein said alkylene, said alkenylene or said alkynylene is optionally substituted with one or more groups independently selected from —$C_{1-4}$ alkyl, —$CF_3$, —CN, —OH, —O($C_{1-4}$ alkyl), —$NH_2$, —NH($C_{1-4}$ alkyl), or —N($C_{1-4}$ alkyl)($C_{1-4}$ alkyl), and further wherein one or more —$CH_2$— units comprised in said alkylene, said alkenylene or said alkynylene are each optionally replaced by a group independently selected from —O—, —NH—, —N($C_{1-4}$ alkyl)-, —CO—, —CO—NH—, —NH—CO—, —S—, —SO—, or —$SO_2$—;

$R^1$ is independently selected from $C_{1-4}$ alkyl, halogen, —$CF_3$, —CN, —OH, —O($C_{1-4}$ alkyl), —$NH_2$, —NH($C_{1-4}$ alkyl), or —N($C_{1-4}$ alkyl)($C_{1-4}$ alkyl), a 5 to 7-membered, saturated or unsaturated carbon ring structure wherein optionally one to three of the carbon atoms are replaced by N, O, or S, said ring structure being optionally substituted with $C_{1-4}$ alkyl, halogen, —$CF_3$, —CN, —OH, —O($C_{1-4}$ alkyl), —$NH_2$, —NH($C_{1-4}$ alkyl), or —N($C_{1-4}$ alkyl)($C_{1-4}$ alkyl), or a aryl or heteroaryl optionally substituted with $C_{1-4}$ alkyl, halogen, —$CF_3$, —CN, —OH, —O($C_{1-4}$ alkyl), —$NH_2$, —NH($C_{1-4}$ alkyl), or —N($C_{1-4}$ alkyl)($C_{1-4}$ alkyl);

$R^2$ is optionally substituted aryl or optionally substituted heteroaryl but not pyrazolyl, wherein said aryl or said heteroaryl may be substituted with one or more groups independently selected from $C_{1-4}$ alkyl, halogen, —$CF_3$, —CN, —OH, —O($C_{1-4}$ alkyl), —$NH_2$, —NH($C_{1-4}$ alkyl), or —N($C_{1-4}$ alkyl)($C_{1-4}$ alkyl), or $R^2$ is pyrazolyl optionally substituted with one or more groups independently selected from $C_{1-4}$ alkyl, halogen, —$CF_3$, —CN, —O($C_{1-4}$ alkyl), —$NH_2$, —NH($C_{1-4}$ alkyl), or —N($C_{1-4}$ alkyl)($C_{1-4}$ alkyl);

$R^3$ is $C_{1-10}$ alkylene, $C_{2-10}$ alkenylene, or $C_{2-10}$ alkynylene, wherein said alkylene, said alkenylene or said alkynylene is optionally substituted with one or more groups independently selected from halogen, —$CF_3$, —CN, —OH, —O($C_{1-4}$ alkyl), —$NH_2$, —NH($C_{1-4}$ alkyl), or —N($C_{1-4}$ alkyl)($C_{1-4}$ alkyl), and further wherein one or more —$CH_2$— units comprised in said alkylene, said alkenylene or said alkynylene are each optionally replaced by a group independently selected from —O—, —NH—, —N($C_{1-4}$ alkyl)-, —CO—, —CO—NH—, —NH—CO—, —S—, —SO—, or —$SO_2$—;

m is an integer of 0 to 8; and each $R^4$ is independently selected from $C_{1-4}$ alkyl, halogen, —$CF_3$, —CN, —OH, —O($C_{1-4}$ alkyl), —$NH_2$, —NH($C_{1-4}$ alkyl), or —N($C_{1-4}$ alkyl)($C_{1-4}$ alkyl); and $R^5$ is aryl or heteroaryl;

$R^5$ is preferably selected from optionally substituted phenyl, benzyl, pyridinyl, pyrazinyl, pyrimidinyl, pyridazinyl, pyrazolyl, imidazolyl, pyrrolyl, triazinyl, tetrazolyl, thiophenyl (thienyl), thiazolyl, furanyl (furyl), furazanyl, oxazolyl, isoxazolyl, benzthienyl, benzfuryl, benzimidazolyl, benzthiazolyl, isothiazolyl, benzisothiazolyl, benzoxazolyl, benzisoxazolyl, isothiazolyl, benztriazolyl, thiadiazolyl, oxadiazolyl, indolyl indazolyl, chinolinyl, naphthyl, anthracenyl. Further preferably, R5 is selected from optionally substituted phenyl, thienyl, indolyl, indolinyl, methylindolyl, piperidinyl. Most preferably, R5 is optionally substituted phenyl.

Further preferably, $R^2$ is selected from optionally substituted phenyl, benzyl, pyridyl, furanyl, thiophenyl, pyrrolyl. Also preferably, $R^2$ is selected from optionally substituted pyrrazolyl, pyridinyl, thienyl, and furanyl. More preferably, $R^2$ is selected from optionally substituted phenyl. The term "optionally substituted" has the meaning given for the structure to which it relates as defined in the claims. For instance, when referring to optionally substituted $R^2$, the optional substituents as defined in the claims, particularly claim 1, for $R^2$ are intended. Further preferably, $R^2$ is selected from among

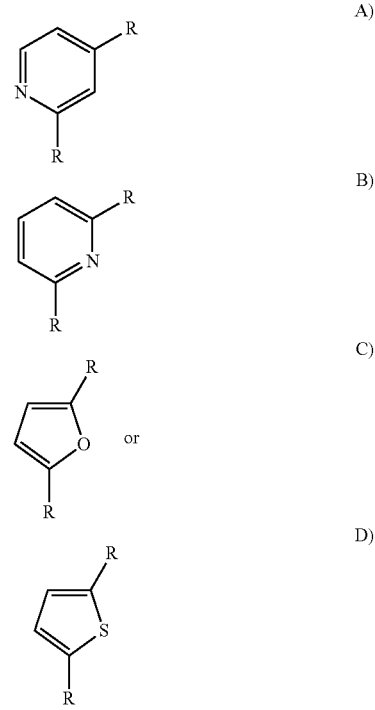

wherein R signifies the point of attachment to the structure of formula (I). More preferably, R2 and R5 are optionally substituted phenyl. Further preferably, R2 and R5 are both unsubstituted phenyl. R3 is preferably —NH—CO—N(CH3)2, preferably attached to the $R^2$ ring structure at the meta position relative to the benzyl ring in formula (I). Preferably, $L^1$ is a bond and $R^1$ is —N(CH3)2. Also preferably, R2 is optionally substituted phenyl, L1 is a bond and R5 is optionally substituted piperidine. R1 is preferably —O—CH2-CH3. More preferably, R1 is —N(CH3)2. R3 is preferably —CO—O—CH2-CH3. More preferably, R3 is —NH—CO—N(CH3)2.

Also contemplated within the invention is a pharmaceutical composition comprising a compound as described herein above. Preferably, the compound is one wherein R2 and/or R5 are optionally substituted phenyl. Further preferably, $L^1$ is a bond and $R^1$ is —N(CH3)2. Also preferably, R2 is optionally substituted phenyl, L1 is a bond and R5 is optionally substituted piperidine. R1 is preferably —O—CH2-CH3. More preferably, R1 is —N(CH3)2. R3 is preferably —CO—O—CH2-CH3. More preferably, R3 is —NH—CO—N(CH3)2. The composition is preferably useful in the treatment, prevention, amelioration, or inhibition of cachexia, atherosclerosis, stroke, coronary artery disease, type II diabetes, and/or disorders and/or conditions associated or related thereto.

The compound preferably has lipase inhibitory activity. Such activity may be measured by methods described hereinabove and below. For example, the method described in example 3, 4 or 5 and/or the Figures referred to therein (e.g., FIG. 1) may be used. The compound preferably has an IC50 of less than 200 uM, less than 100 uM, 40, or 14 micromolar. Further preferably, the IC 50 of the compound is less than 1 micromolar.

The compound preferably inhibits ATGL or an enzymatically active portion thereof. The inhibition is preferably selective. Selectivity may be measured by methods known to the skilled person. For example, the methods described herein in example 4 and/or FIG. 2 may be used. The inhibition of another lipase (e.g. of HSL) is preferably at least 10%, 15%, 30%, 50%, 70% or at least 90% weaker than that observed for ATGL. The compound preferably leads to lowering of blood FFA levels in vivo. Methods of measuring the effect of a compound on blood FFA levels are known to the skilled artisan. For example, the method described herein in example 1 and/or FIG. 4 may be used. Also preferably, the compound does not lead to substantially altered blood glucose levels in vivo. For instance, blood glucose levels may be changed less than 80%, 65%, 50%, 40%, 30%, 20% or 10%. Blood glucose levels may be measured as known to the skilled person; for example, the method described herein in example 1 may be used. The compound preferably does not lead to a reduction in muscle mass in vivo. Methods of measuring muscle mass are known to the skilled artisan. For example, the methods described in Das, 2011, may be used. Preferably, administration of the compound leads to accumulation of muscle mass or inhibition of loss of muscle mass. This is especially preferred when the compound is used in the treatment or prevention of cachexia or an associated disorder.

Further preferably, the compound has a low or absent toxicity. Methods of measuring toxicity are known to the skilled person. Preferably, the method described herein in example 1 "toxicity test" is used. The viability of the cells, measured in OD units, preferably does not change or rises when administering the compound. Also preferably, the viability is reduced by less than 80%, 70%, 50%, 40%, 30%, 20%, 15%, 10% or 5%. Also preferably, the compound exhibits binding affinity for a lipase, which is preferably, MGL, HSL or ATGL, more preferably ATGL or an enzymatically active portion thereof. The binding affinity may be measured as known in the art. Preferably, affinity is measured as described hereinbelow. Preferably, binding affinity is in the micromolar range, more preferably below 100 micromolar, below 70 micromolar, below 40 micromolar, below 25 micromolar, below 14 micromolar, below 10 micromolar, below 5 micromolar, or below 1 micromolar.

Using a compound of formula (I), or a preferred embodiment thereof, the skilled artisan may according to the invention conduct a screening for compounds with desirable and/or improved properties. For instance, the method described in example 7 may be used. Also, further methods used as known in the art may be used.

The invention also relates to the use of compound of formula (I) as disclosed herein in the treatment or prevention of a disorder resulting from high triglyceride levels, cachexia, or its associated or related disorders or conditions, including weight loss, muscle atrophy or wasting, fat loss, reduced WAT, diabetes type II, stroke, atherosclerosis, and coronary artery disease. Generally, the invention relates to the use of compound of formula (I) as disclosed herein for inhibiting the activity of a lipase in vitro, by contacting said lipase with the compound. As noted, in these uses, the compound of formula (I) may be provided in a pharmaceutical composition. Thus, the invention relates to the use of compound of formula (I) as disclosed herein for preparing a pharmaceutical composition for the treatment or prevention of a disorder as disclosed herein.

The invention further provides a method for inhibiting the activity of a lipase in vitro, by contacting the lipase with a compound as defined hereinabove and below. The lipase is preferably HSL, MGL, or ATGL, more preferably ATGL. The inhibition may be advantageously used in in vitro assays, for instance when activity of ATGL is not desired or in order to find out what activity of ATGL contributes to an observed phenomenon.

The invention further provides a method for binding of a compound of the invention to a lipase in vitro, by contacting the lipase with a compound as defined hereinabove and below. The lipase is preferably HSL, MGL, or ATGL, more preferably ATGL. The binding may be advantageously used in in vitro assays, for instance, where the compound comprises a label or is labeled and it is desired to locate ATGL within a cellular, tissue, or organ structure. Thus, also variants of the compound as defined herein, which are labeled, are contemplated within the invention. Using a compound of the invention, such labeled compounds may be prepared by methods known to the skilled person. For instance, the methods described hereinbelow may be used.

In one aspect, the present invention relates to a method for providing further compounds useful in inhibiting lipases, in particular ATGL.

More particularly, the invention relates to a method for identifying a compound that inhibits ATGL comprising:
(a) contacting a population of mammalian cells with one or more compound of formula (I), and
(b) measuring the inhibitory effect of the compound on TG hydrolysis by ATGL.

In particular the inhibition of the release of free fatty acid from TG may be assessed. Preferably, inhibition of ATGL activity is assessed as described in example 7. More preferably, the inhibition of ATGL is specific and the compound identified does not inhibit other lipases to the same degree. Specificity may be assessed by methods known to the skilled artisan. Preferably, the method described in example 7 and FIG. 4 herein is used. Further preferably, the compound inhibits other lipases, such as for example HSL, to a substantially lesser degree than it inhibit ATGL. The inhibition of said other lipase may be at least 15%, 30%, 50%, 70% or 90% weaker as that observed for ATGL inhibition.

Further, the invention relates to a method for identifying an agent or compound that alleviates cachexia, stroke, atherosclerosis, coronary artery disease, diabetes or its associated physiology whereby said agent or compound inhibits ATGL said method comprising:
(a) contacting a population of mammalian cells with one or more compound of formula (I), and
(b) measuring the inhibitory effect of the compound on TG hydrolysis.

In particular the inhibition of the release of free fatty acid from TG may be assessed. Preferably, inhibition of ATGL activity is assessed as described in example 7. More preferably, the inhibition of ATGL is specific and the compound identified does not inhibit other lipases to the same degree. Further preferably, the compound inhibits other lipases to a substantially lesser degree. The inhibition of said other lipases may be at least 15%, 30%, 50%, 70% or 90% weaker as that observed for ATGL.

In a further aspect of the present invention said method is used to identify a compound that inhibits lipolysis, particularly inhibits ATGL activity or expression. In particular the inhibition of the release of free fatty acid from TG may be assessed.

The present assay method may be practiced in vitro, using ATGL or an enzymatically active portion thereof.

The binding affinity of the compound with ATGL can be measured by methods known in the art, such as using surface plasmon resonance biosensors (Biacore), by saturation binding analysis with a labeled compound (e.g. Scatchard and Lindmo analysis), by differential UV spectrophotometer, fluorescence polarization assay, Fluorometric Imaging Plate Reader (FLIPR®) system, Fluorescence resonance energy transfer, and Bioluminescence resonance energy transfer. The binding affinity of compounds can also be expressed in dissociation constant (Kd) or as $IC_{50}$ or $EC_{50}$. The $IC_{50}$ represents the concentration of a compound that is required for 50% inhibition of binding of another ligand to the polypeptide. The $EC_{50}$ represents the concentration required for obtaining 50% of the maximum effect in any assay that measures ATGL function. The dissociation constant, Kd, is a measure of how well a ligand binds to the polypeptide, it is equivalent to the ligand concentration required to saturate exactly half of the binding-sites on the polypeptide. Compounds with a high affinity binding have low Kd, $IC_{50}$ and $EC_{50}$ values, i.e. in the range of 100 nM to 1 pM; a moderate to low affinity binding relates to a high Kd, $IC_{50}$ and $EC_{50}$ values, i.e. in the micromolar range.

One embodiment of the present method for identifying a compound that inhibits cachexia, and its associated or related disorders and conditions, comprises culturing a population of mammalian cells expressing ATGL, determining a first level of FA release from TG or of ATGL activity or expression in said population of cells; exposing said population of cells to a compound, or a mixture of compounds; determining a second level of FA release from TG or of ATGL activity or expression in said population of cells under the same or commensurate conditions, during or after exposure of said population of cells to said compound, or the mixture of said compounds; and identifying the compound(s) that suppress TG hydrolysis and/or ATGL activity or expression. In a specific embodiment, the cells are adipose cells. In a specific embodiment the cells are human cells.

The release of FA from TG or lipolysis or lipase activity or ATGL activity can be determined by methods known in the art such as the methods as described herein. The assay method may be based on the particular expression or activity of the ATGL polypeptide, including but not limited to an enzyme activity. Thus, assays for the enzyme targets may be based on enzymatic activity or enzyme expression. The measurable phenomenon, activity or property may be selected or chosen by the skilled artisan. The person of ordinary skill in the art may select from any of a number of assay formats, systems or design one using his knowledge and expertise in the art. Specific methods to determine the inhibition by a compound by measuring the cleavage of the substrate by the polypeptide ATGL, which is a lipase, are well known in the art.

In one particular embodiment the methods of the present invention further comprise the step of contacting the population of cells with an agonist of the polypeptide. For instance, the activity of the ATGL enzyme can be enhanced by adding the endogenous activator cgi-58. This improves assay quality in cases where extracts lacking sufficient cgi-58 or purified enzyme are used. By using an agonist the polypeptide may be triggered, enabling a proper read-out if the compound inhibits the polypeptide. Similar considerations apply to the measurement of the release of FA from TG. In a particular embodiment, the cells used in the present method are mammalian adipocytes.

In a particular aspect of the present invention the methods include the additional step of comparing the compound to be tested to a control, where the control is a population of cells that have not been contacted with the test compound. In a particular aspect of the present invention the methods described above include the additional step of comparing the compound to be tested to a control, where the control is a population of cells that do not express said polypeptide.

In a particular aspect of the present invention the methods described above include the additional step of comparing the compound to be tested to a control, where the control may be a general lipase inhibitor such as a pancreatric lipase inhibitor, or preferably, a lipase inhibitor such as orlistat.

According to another preferred embodiment, the assay method uses a compound of formula (I) identified as having a binding affinity for the ATGL, and/or has already been identified as having down-regulating activity such as antagonist activity for the target. In vivo animal models of cachexia or wasting conditions or infections or other disorders wherein body weight loss or muscle atrophy is seen may be utilized by the skilled artisan to further or additionally screen, assess, and/or verify the agents or compounds identified in the present invention, including further assessing target/ATGL modulation in vivo. Such animal models include, but are not limited to cachexia models, such as tumor models or AIDS models.

The present invention also provides biologically compatible, inhibiting or modulating compositions comprising an effective amount of one or more compounds identified as target inhibitors, and/or the expression-inhibiting agents as described hereinabove.

A biologically compatible composition is a composition, that may be solid, liquid, gel, or other form, in which the compound, of the invention is maintained in an active form, e.g., in a form able to effect a biological activity. For example, a compound of the invention would have antagonist activity on the ATGL.

A particular biologically compatible composition is an aqueous solution that is buffered using, e.g., Tris, phosphate, or HEPES buffer, containing salt ions. Usually the concentration of salt ions will be similar to physiological levels.

Biologically compatible solutions may include stabilizing agents and preservatives. In a more preferred embodiment, the biocompatible composition is a pharmaceutically acceptable composition. Such compositions can be formulated for administration by topical, oral, parenteral, intranasal, subcutaneous, intraperitoneal, and intraocular, routes. Parenteral administration is meant to include intravenous injection, intramuscular injection, intraarterial injection or infusion techniques. The composition may be administered parenterally in dosage unit formulations containing standard, well-known non-toxic physiologically acceptable carriers, adjuvants and vehicles as desired.

A particular embodiment of the present composition invention is a pharmaceutical composition comprising a therapeutically effective amount of an expression-inhibiting agent as described hereinabove, in admixture with a pharmaceutically acceptable carrier. Another particular embodiment is a pharmaceutical composition for the treatment or prevention of a disease or condition involving cachexia, coronary artery disease, stroke, atherosclerosis, or type 2 diabetes, and its associated or related disorders and conditions, or a susceptibility to such conditions, comprising an effective amount of the ATGL antagonist or inverse agonist of formula (I), its pharmaceutically acceptable salts, hydrates, solvates, or prodrugs thereof in admixture with a pharmaceutically acceptable carrier. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. Pharmaceutical compositions for oral use can be prepared by combining active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl-cellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate. Dragee cores may be used in conjunction with suitable coatings, such as concentrated sugar solutions, which may also contain gum arabic, talc, polyvinyl-pyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

The invention also relates to the use of the compounds disclosed herein for the preparation of pharmaceutical compositions for the treatment or prevention of various conditions.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Preferred sterile injectable preparations can be a solution or suspension in a non-toxic parenterally acceptable solvent or diluent. Examples of pharmaceutically acceptable carriers are saline, buffered saline, isotonic saline (e.g. monosodium or disodium phosphate, sodium, potassium; calcium or magnesium chloride, or mixtures of such salts), Ringer's solution, dextrose, water, sterile water, glycerol, ethanol, and combinations thereof 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The agents or compositions of the invention may be combined for administration with or embedded in polymeric carrier(s), biodegradable or biomimetic matrices or in a scaffold. The carrier, matrix or scaffold may be of any material that will allow composition to be incorporated and expressed and will be compatible with the addition of cells or in the presence of cells. Particularly, the carrier matrix or scaffold is predominantly non-immunogenic and is biodegradable. Examples of biodegradable materials include, but are not limited to, polyglycolic acid (PGA), polylactic acid (PLA), hyaluronic acid, catgut suture material, gelatin, cellulose, nitrocellulose, collagen, albumin, fibrin, alginate, cotton, or other naturally-occurring biodegradable materials. It may be preferable to sterilize the matrix or scaffold material prior to administration or implantation, e.g., by treatment with ethylene oxide or by gamma irradiation or irradiation with an electron beam. In addition, a number of other materials may be used to form the scaffold or framework structure, including but not limited to: nylon (polyamides), dacron (polyesters), polystyrene, polypropylene, polyacrylates, polyvinyl compounds (e.g., polyvinylchloride), polycarbonate (PVC), polytetrafluoroethylene (PTFE, teflon), thermanox (TPX), polymers of hydroxy acids such as polylactic acid (PLA), polyglycolic acid (PGA), and polylactic acid-glycolic acid (PLGA), polyorthoesters, polyanhydrides, polyphosphazenes, and a variety of polyhydroxyalkanoates, and combinations thereof. Matrices suitable include a polymeric mesh or sponge and a polymeric hydrogel. In the particular embodiment, the matrix is biodegradable over a time period of less than a year, more particularly less than six months, most particularly over two to ten weeks. The polymer composition, as well as method of manufacture, can be used to determine the rate of degradation. For example, mixing increasing amounts of polylactic acid with polyglycolic acid decreases the degradation time. Meshes of polyglycolic acid that can be used can be obtained commercially, for instance, from surgical supply companies (e.g., Ethicon, N.J). In general, these polymers are at least partially soluble in aqueous solutions, such as water, buffered salt solutions, or aqueous alcohol solutions that have charged side groups, or a monovalent ionic salt thereof.

The composition medium can also be a hydrogel, which is prepared from any biocompatible or non-cytotoxic homo- or hetero-polymer, such as a hydrophilic polyacrylic acid polymer that can act as a drug absorbing sponge. Certain of them, such as, in particular, those obtained from ethylene and/or propylene oxide are commercially available. A hydrogel can be deposited directly onto the surface of the tissue to be treated, for example during surgical intervention.

Embodiments of pharmaceutical compositions of the present invention comprise a vector encoding an agent of the present invention, particularly a recombinant replication defective vector, and a transfection enhancer, such as poloxamer. An example of a poloxamer is Poloxamer 407, which is commercially available (BASF, Parsippany, N.J.) and is a non-toxic, biocompatible polyol. A poloxamer impregnated with recombinant viruses may be deposited directly on the surface of the tissue to be treated, for example during a surgical intervention. Poloxamer possesses essentially the same advantages as hydrogel while having a lower viscosity.

The active expression-inhibiting agents may also be entrapped in microcapsules prepared, for example, by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (1980) 16th edition, Osol, A. Ed.

Sustained-release preparations may be prepared. Suitable examples of sustained-release preparations include semi-permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

As defined above, therapeutically effective dose means that amount of a compound of formula (I) which ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio of toxic to therapeutic effects is the therapeutic index, and it can be expressed as the ratio, $LD_{50}/ED_{50}$. Pharmaceutical compositions that exhibit large therapeutic indices are preferred. The data obtained from cell culture assays and animal studies are used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. The exact dosage is chosen by the individual physician in view of the patient to be treated. Dosage and administration are adjusted to provide sufficient levels of the active moiety or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The pharmaceutical compositions according to this invention may be administered to a subject by a variety of methods. They may be added directly to target tissues, complexed with cationic lipids, packaged within liposomes, or delivered to target cells by other methods known in the art. Localized administration to the desired tissues may be done by direct injection, transdermal absorption, catheter, infusion pump or stent. The DNA, DNA/vehicle complexes, or the recombinant virus particles are locally administered to the site of treatment. Alternative routes of delivery include, but are not limited to, intravenous injection, intramuscular injection, subcutaneous injection, aerosol inhalation, oral (tablet or pill form), topical, systemic, ocular, intraperitoneal and/or intrathecal delivery. Examples of ribozyme delivery and administration are provided in Sullivan et al. WO 94/02595.

The present invention also provides a method of treating and/or preventing cachexia, and its associated or related disorders and conditions, including weight loss, muscle atrophy or wasting, and reduction of WAT, a pharmaceutical composition or compound as described herein, particularly a therapeutically effective amount of an agent which inhibits the expression or activity of ATGL. In a particular embodiment, the disease is cancer cachexia, wasting disease associated with AIDS or other infectious disease or condition, chronic substance abuse, alcoholism, cirrhosis of the liver, or low body weight associated with anorexia or other disorders. Further, the invention provides said method for the treatment of stroke, atherosclerosis, coronary artery disease, and diabetes. Preferably, the diabetes is diabetes type II.

Administration of the agent or pharmaceutical composition of the present invention to the subject patient includes both self-administration and administration by another person. The patient may be in need of treatment for an existing disease or medical condition, or may desire prophylactic treatment to prevent or reduce the risk for diseases and medical conditions characterized by cachexia, and its associated or related disorders and conditions. The agent of the present invention may be delivered to the subject patient orally, transdermally, via inhalation, injection, nasally, rectally or via a sustained release formulation.

The polypeptides or the polynucleotides of the present invention employed in the methods described herein may be free in solution, affixed to a solid support, borne on a cell surface, or located intracellularly. To perform the methods it is feasible to immobilize either the polypeptide of the present invention or the compound to facilitate separation of complexes from uncomplexed forms of the polypeptide, as well as to accommodate automation of the assay. Interaction (e.g., binding) of the polypeptide of the present invention with a compound can be accomplished in any vessel suitable for containing the reactants. Examples of such vessels include microtitre plates, test tubes, and microcentrifuge tubes. In one embodiment, a fusion protein can be provided which adds a domain that allows the polypeptide to be bound to a matrix. For example, the polypeptide of the present invention can be "His" tagged, and subsequently adsorbed onto Ni-NTA microtitre plates, or ProtA fusions with the polypeptides of the present invention can be adsorbed to IgG, which are then combined with the cell lysates (e.g., $^{(35)}$S-labelled) and the candidate compound, and the mixture incubated under conditions favorable for complex formation (e.g., at physiological conditions for salt and pH). Following incubation, the plates are washed to remove any unbound label, and the matrix is immobilized. The amount of radioactivity can be determined directly, or in the supernatant after dissociation of the complexes. Alternatively, the complexes can be dissociated from the matrix, separated by SDS-PAGE, and the level of the protein binding to the protein of the present invention quantitated from the gel using standard electrophoretic techniques.

Other techniques for immobilizing protein on matrices can also be used in the method of identifying compounds. For example, either the polypeptide of the present invention or the compound can be immobilized utilizing conjugation of biotin and streptavidin. Biotinylated protein molecules of the present invention can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the polypeptides of the present invention but which do not interfere with binding of the polypeptide to the compound can be derivatized to the wells of the plate, and the polypeptide of the present invention can be trapped in the wells by antibody conjugation. As described above, preparations of a labeled candidate compound are incubated in the wells of the plate presenting the polypeptide of the present invention, and the amount of complex trapped in the well can be quantitated.

The polynucleotides encoding ATGL and HSL encoding polynucleotides, particularly ATGL encoding nucleotides, such as human or mouse ATGL are available to the skilled person. For instance, WO2010115825 describes, in FIG. 7 therein, the amino acid and nucleic acid sequence of human ATGL and in FIG. 8 therein the amino acid and nucleic acid sequence of mouse ATGL. WO2010115825 further describes methods of expressing said lipases and conducting assays to test for lipase activity which may be advantageously used in the practice of the current invention.

EXAMPLES

Example 1

Methods cDNA cloning and transient expressions of recombinant His-tagged proteins in COS-7 cells and 3T3-L1 adipocytes.

The coding sequences of mouse ATGL and HSL are amplified by PCR from cDNA prepared from mRNA of mouse white adipose tissue by reverse transcription. The open reading frame, flanked by KpnI/XhoI sites for ATGL and HSL were cloned into the eucaryotic expression vector pcDNA4/HisMax (Invitrogen). Transfection of COS-7 cells was performed with METAFECTENE™ (Biontex) according to the manufacturer's description. The PCR primers used to generate these probes were as follows.

```
ATGL forward
                                            (SEQ ID NO: 1)
5'-TGGTACCGTTCCCGAGGGAGACCAAGTGGA-3', ATGL reverse
                                            (SEQ ID NO: 2)
5'-CCTCGAGCGCAAGGCGGGAGGCCAGGT-3'.

HSL forward
                                            (SEQ ID NO: 3)
5'-TGGTACCT-ATGGATTTACGCACGATGACACA-3', HSL reverse
                                            (SEQ ID NO: 4)
5'-CCTCGAGCGTTCAGTGGTGCAGCAGGCG-3'.
```

Construction of the Recombinant Adenovirus for ATGL Expression (ATGL-Ad) and Infection of 3T3-L1 Cells:

The recombinant adenovirus coding for mouse ATGL is prepared by cotransfection of the shuttle plasmid pAvCvSv containing the ATGL cDNA and pJM 17 into HEK-293 cells. The 1.65 kb Mlu I-Cla I flanked mouse ATGL cDNA fragment (His-tag included) is amplified by PCR from the eucaryotic expression vector pcDNA4/HisMax containing mouse ATGL cDNA and subcloned into Mlu I-Cla I digested pAvCvSv. The resulting shuttle plasmid is cotransfected with pJM 17 into HEK-293 cells using the calcium phosphate coprecipitation method. Large scale production of high titer recombinant ATGL-Ad is performed as described elsewhere. 3T3-L1 fibroblasts were cultured in DMEM containing 10% FCS and differentiated using a standard protocol (Bernlohr, D. A. et al (1985) J Biol Chem 260: 5563-7). Adipocytes are infected on day 8 of differentiation with a multiplicity of infection (moi) of 400 plaque forming units/cell. For that purpose appropriate pfu are preactivated in DMEM containing 0.5 µg/ml of polylysin for 100 min and afterwards the cells are incubated with this virus suspension for 24 hours. After 24 h the medium is removed and the cells are incubated for further 24 h with complete medium. For most of the experiments, recombinant adenovirus expressing β-galactosidase was used as a control (LacZ-Ad).

Western Analysis.

Cellular proteins are separated by SDS-polyacrylamide gel electrophoresis and transferred to a nitrocellulose membrane (Schleicher & Schuell, Germany). For detection of His-tagged proteins, blots were incubated with $\frac{1}{10000}$ diluted Anti-His monoclonal antibody (6×His, Clonetech). Bound immunoglobulins are detected with a HRP-labeled IgG conjugates (Vector Inc.) and visualized by ECL detection (ECL plus, Amersham Pharmacia Biotech, Germany) on a Storm Image Analysis system. Quantitation is performed using ImageQuant Software.

Reaction of ATGL and HSL with the fluorescent lipase inhibitor NBD-HEHP. Transfected COS-7 cells are washed twice with PBS, scraped into lysis buffer (0.25 M sucrose, 1 mM EDTA, 1 mM dithioerythritol, 20 µg/ml leupeptin, 2 µg/ml antipain, 1 µg/ml pepstatin) and disrupted on ice by sonication. Nuclei and unbroken materials are removed by centrifugation at 1.000 g at 4° C. for 15 min to obtain cytoplasmatic extracts. 50 µg of protein is incubated with 1 nmol fluorescently labelled lipase inhibitor O-((6-(7-Nitrobenz-2-oxa-1,3-diazol-4-yl)amino)hexanoyl)aminoethyl-O-(n-hexyl)phosphonic acid p-nitrophenyl ester (NBD-HEHP) (Oskolkova, O. V. et al (2003) Chem Phys Lipids 125:103-14.) and 1 mM Triton X-100 (especially purified for membrane research, Hofmann LaRoche) at 37° C. for 2 hours under shaking. Protein is precipitated with 10% TCA for 1h on ice, washed with acetone and separated by 10% SDS-PAGE. Gels are fixed in 10% ethanol and 7% acetic acid. Fluorescence is detected with a BioRad FX Pro Laser scanner (excitation 488 nm, emission 530 nm).

Northern Analysis.

The cDNA probe for northern blot analysis of mouse ATGL is prepared by RT-PCR by use of first-strand cDNA from mouse fat mRNA. PCR primers used to generate this probe are as follows: forward 5'-TGGAACATCTCAT-TCGCTGG-3' (SEQ ID NO: 5), reverse 5'-AATGCCGC-CATCCACATAG-3' (SEQ ID NO: 6). Total RNA was isolated from various mouse tissues using the TRI Reagent procedure according to manufacturer's protocol (Molecular Research Center, Karlsruhe, Germany). Specific mRNAs were detected using standard Northern blotting techniques with 10 µg total RNA. 32P-labeled probes for hybridization were generated using random priming. Northern blots are visualized by exposure to a PhosphorImager Screen (Apbiotech, Freiburg, Germany) and analyzed using ImageQuant Software.

Compound Synthesis

Compounds 1-4 were prepared using organic synthesis methods. Unless otherwise stated, all experiments were carried out under inert atmosphere by using standard Schlenk-techniques. Acetonitrile, DMF, Ethanol and Dimethoxyethane were purchased as absolute solvents from Acros Organics, Fisher Scientific and Sigma Aldrich. All applied starting materials were commercially available from Alfa Aesar and Sigma Aldrich and were used as received. Silica gel chromatography was performed with Acros Organics silica gel 60 (35-70 µM). $^1$H and $^{13}$C NMR spectra were recorded on Bruker AVANCE III 300 spectrometer ($^1$H: 300.36 MHz; $^{13}$C: 75.53 MHz) and chemical shifts are referenced to residual protonated solvent signals as internal standard. Electron impact (EI, 70 eV) HRMS spectra were recorded on Waters GCT Premier equipped with direct insertion (DI) and GC (HP GC7890A). GC/MS analyses were made on an Agilent Technologies 5975 C inert MSD with Triple Axis Detector GC system with a mass sensitive detector.

Ethyl 1-(4-ethoxyphenyl)-4-hydroxy-1H-pyrazole-3-carboxylate (1)

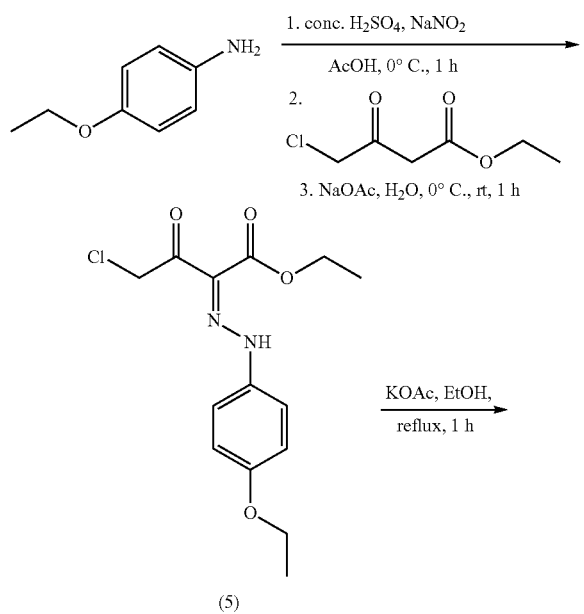

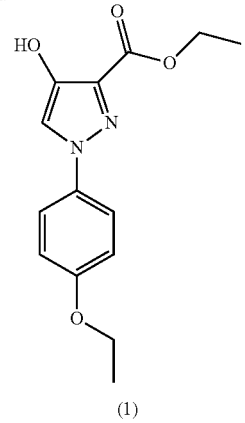

Ethyl-4-chloro-2-((4-ethoxyphenyl)diazenyl)-3-oxobutanoate (5)

A 10 mL one-neck round-bottom flask was charged with 250.0 mg (0.24 mL, 1.825 mmol, 1.04 eq) 4-ethoxyaniline which was dissolved in 3.1 mL acetic acid at 10° C. (ice bath). To this cooled solution 128.0 mg (1.861 mmol, 1.06 eq) NaNO$_2$ in 0.5 mL conc. H$_2$SO$_4$ were added and the reaction mixture was stirred at 10° C. for 1 h. In a second 25 ml one-neck round-bottom flask 288.6 mg (0.24 mL, 1.755 mmol, 1.0 eq) ethyl-4-chloro-3-oxobutanoate were dissolved in a mixture of 1.3 mL acetic acid and 2.6 mL water and cooled to 0° C. (ice bath+NaCl). After one hour stirring at 10° C. the generated solution of the diazonium salt was given to the second solution at 0° C. and stirred for further 15 min at this temperature. An aqueous solution of 1.58 g (19.305 mmol, 11 eq) NaOAc in 3.0 mL water was added to the reaction mixture at 0° C. and the product precipitated. Stirring at rt over night, filtration, washing with a small amount of water and drying under high pressure yielded the crude product which was used in the next reaction step without further purification.

yield: 453.7 mg (83%); yellow-brown solid; M.p.: 106-110° C.; $^1$H-NMR (300 MHz, DMSO-d$_6$): Isomer I (25%): δ (ppm)=14.39 (s, 1H, NH), 7.57-7.35 (m, 2H, Ar—H), 7.98-7.95 (m, 2H, Ar—H), 4.95-4.92 (m, 2H, Cl—CH$_2$), 4.31-4.27 (m, 2H, CH$_2$), 4.03-3.98 (m, 4H, 2 CH$_2$), 1.34-1.27 (m, 6H, 2 CH$_3$), Isomer II (75%): δ (ppm)=12.35 (s, 1H, NH), 7.57-7.35 (m, 2H, Ar—H), 6.98-6.95 (m, 2H, Ar—H), 4.95-4.92 (m, 2H, Cl—CH$_2$), 4.31-4.27 (m, 2H, CH$_2$), 4.03-3.98 (m, 4H, 2 CH$_2$), 1.34-1.27 (m, 6H, 2 CH$_3$); $^{13}$C-NMR (75.5 MHz, DMSO-d$_6$): Isomer I: δ (ppm)=187.6 (C=O), 164.0 (C=O), 156.9 (C$_q$), 135.2 (C=N), 125.1 (C$_q$), 118.1 (2 CH$_{Ar}$), 115.2 (2 CH$_{Ar}$), 63.2 (OCH$_2$), 60.3 (Cl—CH$_2$), 49.6 (CH$_2$), 14.1 (CH$_3$), 13.9 (CH$_3$), Isomer II: δ (ppm)=185.7 (C=O), 162.0 (C=O), 156.0 (C$_q$), 135.2 (C=N), 125.1 (C$_q$), 117.4 (2 CH$_{Ar}$), 115.1 (2 CH$_{Ar}$), 63.2 (OCH$_2$), 60.8 (Cl—CH$_2$), 46.9 (CH$_2$), 14.5 (CH$_3$), 13.9 (CH$_3$).

Ethyl 1-(4-ethoxyphenyl)-4-hydroxy-1H-pyrazole-3-carboxylate (1)

A 25 mL Schlenk tube was charged with 270.6 mg (0.866 mmol, 1.0 eq) ethyl-4-chloro-2-((4-ethoxyphenyl)diazenyl)-3-oxobutanoate (5) which was suspended in 4 mL EtOH under a gentle stream of nitrogen. After adding 102.0 mg (1.039 mmol, 1.2 eq) KOAc the suspension was stirred under reflux for 1.5 h, during which the suspension dissolved. TLC analysis (CH/EtOAc 3:1) indicated full conversion of the starting material. After cooling to rt the mixture was transferred to a flask to remove the EtOH with a rotary evaporator. The residue was dissolved in 20 mL EtOAc and washed with water (2×15 mL) and 15 mL brine, dried over $MgSO_4$ and concentrated at the rotary evaporator. Drying at high vacuum yielded the pure product without further purification.

yield: 232.4 mg (97%); dark red-brown solid; M.p.: 96-98° C.; $R_f$(CH/EtOAc 3:1): 0.35; $^1$H-NMR (300 MHz, DMSO-$d_6$): δ (ppm)=9.07 (s, 1H, OH), 7.96 (s, 1H, Ar—H), 7.70 (d, $^3J$=9.0 Hz, 2H, Ar—H), 7.03 (d, $^3J$=9.0 Hz, 2H, Ar—H), 4.28 (q, $^3J$=6.9 Hz, 2H, $CH_2$), 4.06 (q, $^3J$=6.9 Hz, 2H, $CH_2$), 1.36-1.27 (m, 6H, 2 $CH_3$); $^{13}$C-NMR (75.5 MHz, DMSO-$d_6$): δ (ppm)=161.6 (C=O), 157.3 ($C_q$), 145.0 ($C_q$—OH), 132.8 ($C_q$), 131.1 ($C_q$), 120.0 (2$CH_{Ar}$), 114.9 (2 $CH_{Ar}$), 114.8 ($CH_{Ar}$), 63.3 ($CH_2$), 59.7 ($CH_2$), 14.5 ($CH_3$), 14.2 ($CH_3$); GC-MS (NM_50_S2): $t_R$=8.071 min (m/z=276.1, 99.0% $M^+$, BP).

Ethyl 1-(4-ethoxyphenyl)-1H-pyrazole-3-carboxylate (2)

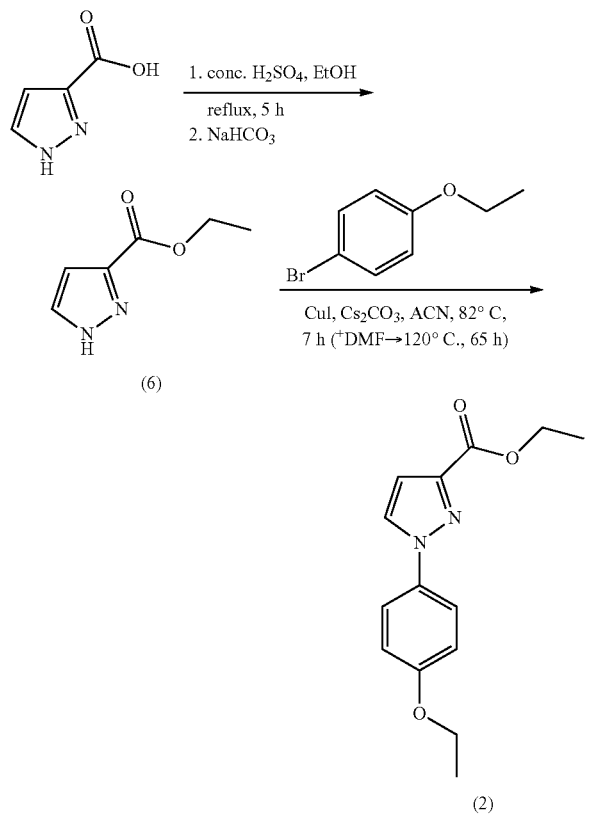

(6)

(2)

Ethyl 1H-pyrazole-3-carboxylate (6)

A 100 mL Schlenk tube was dried under vacuum, filled with nitrogen and charged with 0.5 g (4.461 mmol, 1.0 eq) 1H-pyrazol-3-carboxylic acid which was dissolved in 20 mL EtOH. After adding 1.31 g (0.72 mL, 13.382 mmol, 3.0 eq) conc. $H_2SO_4$ the colorless reaction mixture was heated to reflux (100° C.) and stirred at this temperature for 4 h. TLC analysis (DCM/MeOH 95:5) indicated full conversion of the starting material. After cooling to rt the mixture was transferred to a flask to remove the solvent at a rotary evaporator. The colorless residue was diluted in 20 mL water and neutralized with 17 mL saturated aqueous $NaHCO_3$ solution. Thereby a white solid precipitated. The aqueous layer was extracted with EtOAc (4×50 mL), dried over $MgSO_4$ and the solvent was evaporated under reduced pressure to yield the pure title compound.

yield: 582.5 mg (93%); colorless solid; M.p.: 158-161° C.; $R_f$(DCM/MeOH 95:5): 0.42;

$^1$H-NMR (300 MHz, CDCl$_3$): δ (ppm)=10.69 (bs, 1H, NH), 7.84 (d, $^4J$=2.1 Hz, 1H, Ar—H), 6.86 (d, $^4J$=2.1 Hz, 1H, Ar—H), 4.43 (q, $^3J$=7.2 Hz, 2H, $CH_2$), 1.41 (t, $^3J$=7.2 Hz, 3H, $CH_3$); $^{13}$C-NMR (75.5 MHz, CDCl$_3$): δ (ppm)=161.8 (C=O), 141.6 ($C_q$), 132.3 ($CH_{Ar}$), 107.8 ($CH_{Ar}$), 61.1 ($CH_2$), 14.3 ($CH_3$); GC-MS (NM_50_S2): $t_R$=4.655 min (m/z=140.1, 98.0% $M^+$, BP: 95.0).

Ethyl 1-(4-ethoxyphenyl)-1H-pyrazole-3-carboxylate (2)

A 10 mL Schlenk tube was dried under vacuum, filled with nitrogen and consecutively charged with 19.4 mg (0.102 mmol, 0.2 eq) CuI, 332.3 mg (1.020 mmol, 2.0 eq) $Cs_2CO_3$, 100.0 mg (0.714 mmol, 1.4 eq) ethyl 1H-pyrazole-3-carboxylate (6), 102.4 mg (73.0 µL, 0.510 mmol, 1.0 eq) p-bromophenetol and 1 mL dry ACN. The light brown suspension was degassed by vaccum/$N_2$ cycles and stirred first at 82° C. for 7 h and than after adding 0.5 mL dry DMF (solubility issue) at 120° C. for further 65 h. The GC-MS analysis showed full conversion. ACN and DMF were removed under high pressure and the brown residue was suspended in 10 mL EtOAc. After filtration of the brown suspension through a pad of silica and flushing with 150 mL EtOAc the colorless filtrate was concentrated under reduced pressure leading to 52.1 mg (39%) crude product as a green-brown oil. Final purification by column chromatography (CH/EtOAc 3:1, size: 15.5×2.0 cm, 20 g silica gel) yielded the pure title compound.

yield: 10.2 mg (8%); orange solid; M.p.: 88-90° C.; $R_f$(CH/EtOAc 3:1): 0.40; $^1$H-NMR (300 MHz, DMSO-$d_6$): δ (ppm)=8.51 (d, $^4J$=2.4 Hz, 1H, Ar—H), 7.78 (d, $^3J$=9.0 Hz, 2H, Ar—H), 7.07 (d, $^3J$=9.0 Hz, 2H, Ar—H), 6.97 (d, $^4J$=2.4 Hz, 1H, Ar—H), 4.31 (q, $^3J$=6.9 Hz, 2H, $CH_2$), 4.08 (q, $^3J$=7.2 Hz, 2H, $CH_2$), 1.37-1.29 (m, 6H, 2 $CH_3$); $^{13}$C-NMR (75.5 MHz, DMSO-$d_6$):

δ (ppm)=161.4 (C=O), 157.6 ($C_q$), 143.6 ($C_q$), 132.5 ($C_q$), 129.5 ($CH_{Ar}$), 120.7 (2$CH_{Ar}$), 115.0 (2$CH_{Ar}$), 119.8 ($CH_{Ar}$), 63.4 ($CH_2$), 60.3 ($CH_2$), 14.5 ($CH_3$), 14.1 ($CH_3$); GC-MS (NM_50_S2): $t_R$=7.722 min (m/z=260.1, 98.0% $M^+$, BP).

Ethyl 4'-ethoxybiphenyl-3-carboxylate (3)

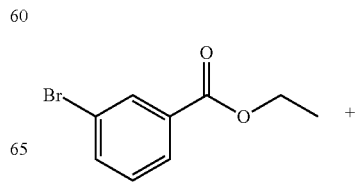 +

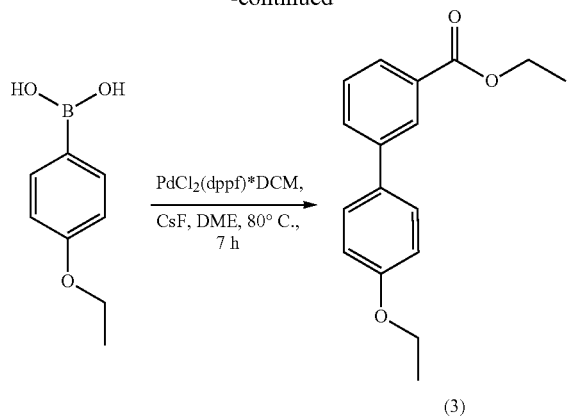

(3)

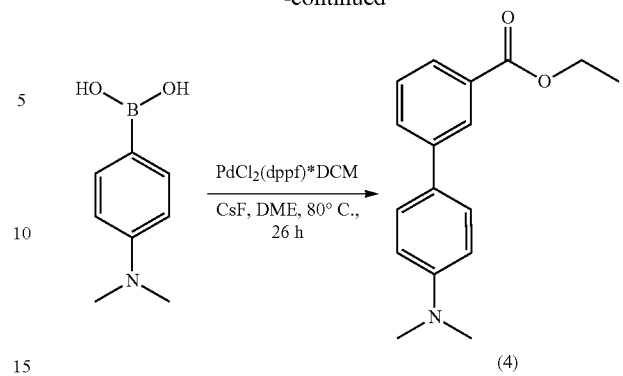

(4)

A 20 mL Schlenk tube was dried under vacuum, filled with nitrogen and charged consecutively with 100.0 mg (70 μL, 0.437 mmol, 1.0 eq) ethyl-3-bromobenzoate, 72.5 mg (0.437 mmol, 1.0 eq) 4-ethoxyphenylboronic acid, 139.3 mg (0.917 mmol, 2.1 eq) CsF, 17.8 mg (0.022 mmol, 0.05 eq) PdCl$_2$(dppf)*DCM and 5.0 mL DME. The orange suspension was degassed by vacuum/N$_2$ cycles and stirred at 80° C. for 7 h. GC-MS analysis indicated full conversion (98% product) of the starting material. The reaction mixture was filtered through a pad of celite which was rinsed with EtOAc. The solvent from the filtrate was removed under reduced pressure and final purification by column chromatography (CH/EtOAc 15:1, size: 12.5×2.0 cm, 15 g silica gel) yielded the pure product.

yield: 109.5 mg (93%); colorless solid; M.p.: 46-47° C.; R$_f$ (CH/EtOAc 15:1): 0.40; $^1$H-NMR (300 MHz, CDCl$_3$): δ (ppm)=δ (ppm)=8.25 (t, $^4$J=1.5 Hz, 1H, Ar—H), 7.98 (d, $^3$J=7.8 Hz, 1H, Ar—H), 7.74 (d, $^3$J=7.8 Hz, 1H, Ar—H), 7.56 (d, $^3$J=9.0 Hz, 2H, Ar—H), 7.48 (t, $^3$J=7.8 Hz, 1H, Ar—H), 6.98 (d, $^3$J=9.0 Hz, 2H, Ar—H), 4.41 (q, $^3$J=7.2 Hz, 2H, CH$_2$), 4.09 (q, $^3$J=6.9 Hz, 2H, CH$_2$), 1.47-1.39 (m, 6H, 2 CH$_3$); $^{13}$C-NMR (75.5 MHz, CDCl$_3$): δ (ppm)=166.6 (C=O), 158.8 (C$_q$), 141.0 (C$_q$), 132.5 (C$_q$), 131.0 (C$_q$), 130.9 (CH$_{Ar}$), 128.7 (CH$_{Ar}$), 128.2 (2 CH$_{Ar}$), 127.7 (CH$_{Ar}$), 127.6 (CH$_{Ar}$), 114.8 (2 CH$_{Ar}$), 63.8 (CH$_2$), 61.0 (CH$_2$), 14.8 (CH$_3$), 14.3 (CH$_3$); GC-MS (NM_50_S2): t$_R$=7.796 min (m/z=270.1, 99% M$^+$, BP); HRMS (EI$^+$): m/z: calcd for C$_{17}$H$_{18}$O$_3$ [M]$^+$: 270.1256; found 270.1260.

Ethyl 4'-(dimethylamino)biphenyl-3-carboxylate (4)

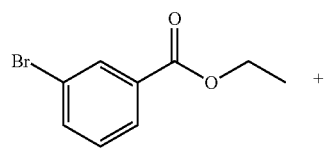 +

A 25 mL Schlenk tube was dried under vacuum, filled with nitrogen and charged consecutively with 150.0 mg (0.1 mL, 0.655 mmol, 1.0 eq) ethyl-3-bromobenzoate, 107.9 mg (0.655 mmol, 1.0 eq) 4-(dimethylamino)phenylboronic acid, 208.9 mg (1.375 mmol, 2.1 eq) CsF, 26.7 mg (0.033 mmol, 0.05 eq) PdCl$_2$(dppf)*DCM and 7.5 mL DME. The orange suspension was degassed by vacuum/N$_2$ cycles and stirred at 80° C. for 26 h. GC-MS analysis indicated full conversion (86% product) of the starting material. The reaction mixture was filtered through a pad of celite which was rinsed with EtOAc. The solvent from the filtrate was removed under reduced pressure and final purification by column chromatography (CH/EtOAc 19:1, size: 14.0×2.0 cm, 25 g silica gel) yielded the pure product.

yield: 135.9 mg (77%); colorless solid; M.p.: 79-81° C.; R$_f$ (CH/EtOAc 19:1): 0.24; $^1$H-NMR (300 MHz, CDCl$_3$): δ (ppm)=8.26 (s, 1H, Ar—H), 7.94 (d, $^3$J=7.8 Hz, 1H, Ar—H), 7.74 (d, $^3$J=7.8 Hz, 1H, Ar—H), 7.55 (d, $^3$J=9.0 Hz, 2H, Ar—H), 7.46 (t, $^3$J=7.8 Hz, 1H, Ar—H), 6.82 (d, $^3$J=9.0 Hz, 2H, Ar—H), 4.41 (q, $^3$J=7.2 Hz, 2H, CH$_2$), 3.01 (s, 6H, 2 CH$_3$), 1.42 (t, $^3$J=7.2 Hz, 3H, CH$_3$); $^{13}$C-NMR (75.5 MHz, CDCl$_3$): δ (ppm)=166.8 (C=O), 150.2 (C$_q$—N(CH$_3$)$_2$), 141.4 (C$_q$), 130.8 (C$_q$), 130.4 (CH$_{Ar}$), 128.6 (CH$_{Ar}$), 128.0 (C$_q$), 127.7 (2 CH$_{Ar}$), 127.2 (CH$_{Ar}$), 127.0 (CH$_{Ar}$), 112.7 (2 CH$_{Ar}$), 60.9 (CH$_2$), 40.5 (N(CH$_3$)$_2$), 14.4 (CH$_3$); GC-MS (NM_50_S2): t$_R$=8.288 min (m/z=269.1, 99% M$^+$, BP).

Expression of recombinant proteins and preparation of cell lysates. Monkey embryonic kidney cells (Cos-7; ATCC CRL-1651) were cultivated in DMEM (GIBCO, Invitrogen Corp., Carlsbad, Calif.), containing 10% fetal calf serum (FCS, Sigma-Aldrich) and antibiotics (100 IU/ml penicillin and 100 μg/ml streptomycin) at standard conditions (37° C., 5% CO$_2$, 95% humidified atmosphere). Cells were transfected with 1 μg DNA complexed to Metafectene (Biontex GmbH, Munich, Germany) in serum free DMEM. After 4 h the medium was replaced by DMEM supplemented with 10% FCS. For the preparation of cell lysates, cells were washed with 1×PBS, collected using a cell scraper, and disrupted in buffer A (0.25 M sucrose, 1 mM EDTA, 1 mM dithiothreitol, 20 μg/ml leupeptine, 2 μg/ml antipain, 1 μg/ml pepstatin, pH 7.0) by sonication (Virsonic 475, Virtis, Gardiner, N.J.). Nuclei and unbroken cells were removed by centrifugation (1,000×g, 4° C., for 10 min).

For over-expression of ATGL and CGI-58 in E. coli (XL-1) cDNA was cloned into the vector pASK-IBA5+ (IBA-BioTagnology). Cells were transformed and cultured over night at 30° C. Thereafter cells were transferred into a fresh medium and grown until OD600 reached 0.7-0.8. Expression was induced using 0.2 μg/ml anhydrotetracycline. After 3 hours incubation at 37° C. cells where harvested, resuspended in lysis buffer (0.25M Sucrose, 1 mM DTT, 1 mM EDTA) and disrupted by sonication. Lysates were centrifuged at 15,000 g for 20 min at 4° C. and the supernatant was collected.

Determination of protein concentrations of cell lysates and detection of His-tagged proteins by Western blotting analysis were performed as described below.

Preparation of tissue homogenates. Murine adipose tissue samples were washed in PBS containing 1 mM EDTA and homogenized on ice in buffer A using an Ultra Turrax (IKA, Staufen, Germany). Homogenates were centrifuged for 30 min at 20,000×g and 4° C. to obtain tissue extracts. Protein content was determined as described below.

Determination of TG hydrolase activity. For the determination of TG hydrolase activity of cell lysates containing various recombinant proteins, tissue extracts, or purified proteins, samples in a total volume of 100 µl buffer A were incubated with 100 µl substrate in a water bath at 37° C. for 60 min. As a control, incubations under identical conditions were performed in buffer A alone. After incubation, the reaction was terminated by adding 3.25 ml of methanol/chloroform/heptane (10:9:7) and 1 ml of 0.1 M potassium carbonate, 0.1 M boric acid, (pH 10.5). After centrifugation (800×g, 15 min), the radioactivity in 1 ml of the upper phase was determined by liquid scintillation counting. Counts from control incubations were subtracted and the rate of FA hydrolysis calculated using $^3$H radiolabelling of triolein substrate. TG substrate was prepared by emulsifying 330 µM triolein (40 000 cpm/nmol) and 45 µM phosphatidylcholine/phosphatidylinositol (3:1) in 100 mM potassium phosphate buffer, (pH 7.0) by sonication and adjusted to 5% essentially FA-free BSA (Sigma, St. Louis, Mo.).

Determination of MG hydrolase activity. Monoacylglycerol hydrolase activities were determined using recombinant, purified mMGL and rac-1-(3)-oleoylglycerol as substrate as described (Taschler, 2011).

Lipolysis of 3T3-L1 cells. 3T3-L1 fibroblasts (CL-173) were obtained from ATCC (Teddington, UK) and cultivated in DMEM containing 4.5 g/liter glucose and L-glutamine (Invitrogen) supplemented with 10% FCS and antibiotics under standard conditions. Cells were seeded in 12 well plates and two days after confluence, medium was changed to DMEM supplemented with 10% FCS containing 10 µg/ml insulin (Sigma-Aldrich), 0.25 µM (0.4 µg/ml) dexamethasone (Sigma-Aldrich), and 500 µM isobutylmethylxanthine (Sigma-Aldrich). After 3 and 5 days, medium was changed to DMEM supplemented with 10% FCS containing 10 µg/ml and 0.5 µg/ml insulin, respectively. On day 7 of differentiation the cells were incubated ON in the absence of insulin. Cells were used at day 8 of differentiation. Therefore cells were preincubated with 0, 0.1, 1, 10, or 50 µM of Atglistatin in the presence or absence of 10 µM Hi 76-0079 (NNC 0076-0000-0079, provided by Novo Nordisk, Denmark) for 2 h. Then, the medium was replaced by DMEM containing 2% BSA (fatty acid free, Sigma, St. Louis, Mo.), 10 µM forskolin, and 0, 0.1, 1, 10, or 50 µM of Atglistatin in the presence or absence of 10 µM Hi 76-0079 for 1h. The release of FFA and glycerol in the media was determined using commercial kits (NEFA C, WAKO, free glycerol reagent, Sigma). Protein concentration was determined using BCA reagent (Pierce) after extracting total lipids using hexane:isopropanol (3:2), and lysing the cells using SDS:NaOH (0.3%:0.1 N).

Lipolysis of isolated WAT organ cultures—Gonadal fat pads of C57Bl6 mice were surgically removed and washed several times with PBS. Tissue pieces (~15 mg) were preincubated in DMEM containing 0, 0.1, 1, 10, and 50 µM Atglistatin for 8 h at C37° C., 5% $CO_2$, 95% humidified atmosphere. Thereafter, the medium was replaced by DMEM containing 2% BSA (fatty acid-free) either in the presence or in the absence of 10 µM forskolin and 0, 0.1, 1, 10, and 50 µM, and incubated for another 60 min at 37° C. Then, aliquots of the medium were removed and analyzed for FFA and glycerol content using commercial kits (HR Series NEFA-HR(2), WAKO Diagnostics, Neuss, Germany; Sigma, St. Louis, Mo.). For protein determinations, fat pads were washed extensively with PBS and lysed in 0.3 N NaOH/0.1% SDS. Protein measurements were performed using the BCA reagent (Pierce Rockford, Ill.).

Toxicity test for Atglistatin in AML-12 mouse hepatocytes. For MTT-based in vitro viability assays, cells were seeded at an initial density of $1 \times 10^4$ cells per well in 96-well plates and cultured under standard conditions for twenty-four hours. The next day, cells were pretreated with different concentrations of Atglistatin dissolved in DMSO or Cisplatin dissolved in dimethylformamide (DMF) (Sigma-Aldrich) as positive control for two hours. Medium was replaced by an identical fresh medium and incubated again for the indicated timepoints. Thereafter cells were incubated for 3 hours with 100 µl Thiazolyl Blue Tetrazolium Bromide (MTT). The resulting violet formazan crystals were dissolved by adding 100 µl of MTT Solubilization Solution (0.1% NP-40, 4 mM HCl and anhydrous isopropanol). After complete dissolution of the formazan product, absorbance was measured at 595 nm and 690 nm. The values obtained at 690 nm were subtracted from the 595 nm measurements.

Animals. Mice (C57Bl/6J) were maintained on a regular light-dark cycle (14 hours light, 10 hours dark) and kept on a standard laboratory chow diet (4.5% wt/wt fat, Sniff GMBH Germany). Maintenance, handling, and tissue collection from mice has been approved by the Austrian Federal Ministry of Science and Research Education and by the ethics committee of the University of Graz. Atglistatin was orally administrated by gavage of 200 µl olive oil containing Atglistatin.

Determination of tissue TG content. For tissue collection mice were euthanized by cervical dislocation. Subsequently, tissues were excised and snap frozen. After homogenisation in buffer A without DTT, TG was measured using TG reagent (Thermo Electron Corp., Victoria, Australia).

Plasma parameters. Blood samples of fed or fasted mice were collected by retro-orbital puncture. Plasma levels of TG, glycerol, FFA, and total cholesterol were determined using commercial kits (Thermo Electron Corp., Victoria, Australia; Sigma, St. Louis, Mo.; Wako Chemicals, Wako Chemicals, Neuss, Germany; Roche Diagnostics, Vienna, Austria). Blood glucose was determined using Accu-Check glucometer (Roche, Diagnostics).

Determination of protein concentrations. Protein concentrations were determined using Bio-Rad protein assay according to the manufacturer's protocol (Bio-Rad 785, Bio-Rad Laboratories, Munich, Germany), using BSA as standard. Alternatively, protein measurements were performed using the BCA reagent (Pierce, Rockford, Ill.).

Statistical Analysis. Statistical analyses were determined by Student's unpaired t-test (two tailed). Following levels of statistical significance were used: * . . . $p<0.05$,  . . . $p<0.01$, and * . . . $p<0.001$.

Example 2

Compound Chemistry

Compound 1 (FIG. 1A) inhibits the activity of recombinant ATGL ($IC_{50}$=50 µM). The HO-group in 4-position could be an anchor point for path II metabolism In order to test the effect of the HO-group in the 4-position on the inhibitory effect and toxicity, compound 2 was prepared by Ullmann-arylation of ethyl pyrazol-3-carboxylate. This compound inhibited ATGL with an $IC_{50}$ of=40 µM. Both compounds showed some limited toxicity in in vitro tests. The pyrazole moiety was therefore targeted for replacement. Next, a series of compounds were prepared in which the pyrazole was replaced by other aromatic and heteroaromatic rings keeping the 1,3-arrangement of the 4-ethoxyphenyl- and ethoxycarbonyl-substituents constant.

Figure 1:
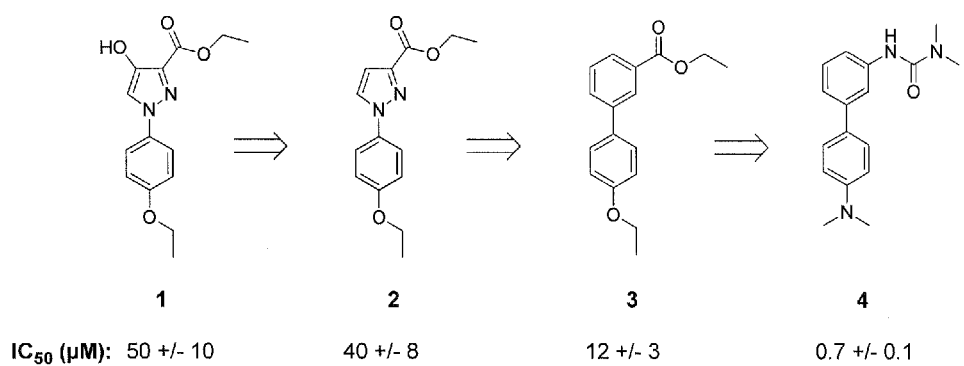
FIG. 1(A) is an illustration of the structure of compounds 1-4 along with their IC50 data.
FIGS. 1(B) and 1(C) are graphs that show the effect of compounds 1-4 on ATGL activity.
Figure 1:
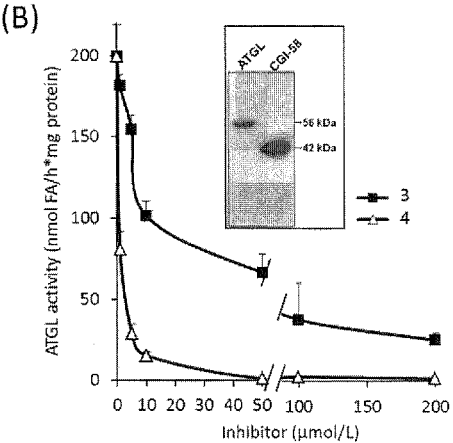
Figure 1:
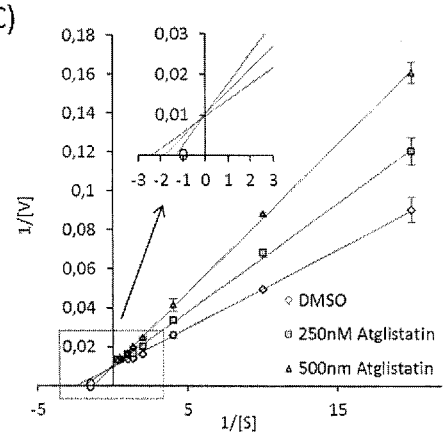

Using this strategy, biphenyl compound 3 ($IC_{50}$=12 µM, FIG. 1) emerged as a suitable scaffold. Next, the role of the ethoxy substituent in the bottom ring was investigated. A series of compounds prepared by Pd-catalyzed Suzuki-coupling of different 4-substituted phenylboronic acids with ethyl-3-bromobenzoate indicated that electron donating groups at the 4'-phenyl position promote ATGL inhibition. Additionally possibilities were surveyed to replace the ester moiety in the 3-position by other functional groups. This resulted in urea compound 4 which showed improved inhibition activity. The dose-dependent inhibition of ATGL activity by compounds 3 and 4 is shown in FIG. 1B. Compound 4 was named Atglistatin and inhibited the activity of recombinant ATGL with an $IC_{50}$ of 0.7 µM. Cytotoxicity assays revealed for 4 only a very moderate decrease in cell viability (tested as described in example 1/methods), at concentrations ≥100 µM.

Example 3

Kinetic Studies of Inhibitor Action

To investigate the mechanism of Atglistatin-mediated ATGL inhibition, kinetic studies were performed by varying substrate and inhibitor concentrations. Kinetic analysis revealed an increase in the apparent $K_m$ values and unchanged $V_{max}$ (FIG. 1C) indicating that Atglistatin acts as a competitive inhibitor. Based on the increase of $K_m$ values determined in three independent experiments and using non-linear regression analysis (SigmaPlot 12.0), a $K_i$ value of 0.5+/−0.2 µM was calculated. However, it has to be considered that this is a relative value, since the TG substrate is not water-soluble and consequently only partially available for the reaction.

Example 4

Figure 2:
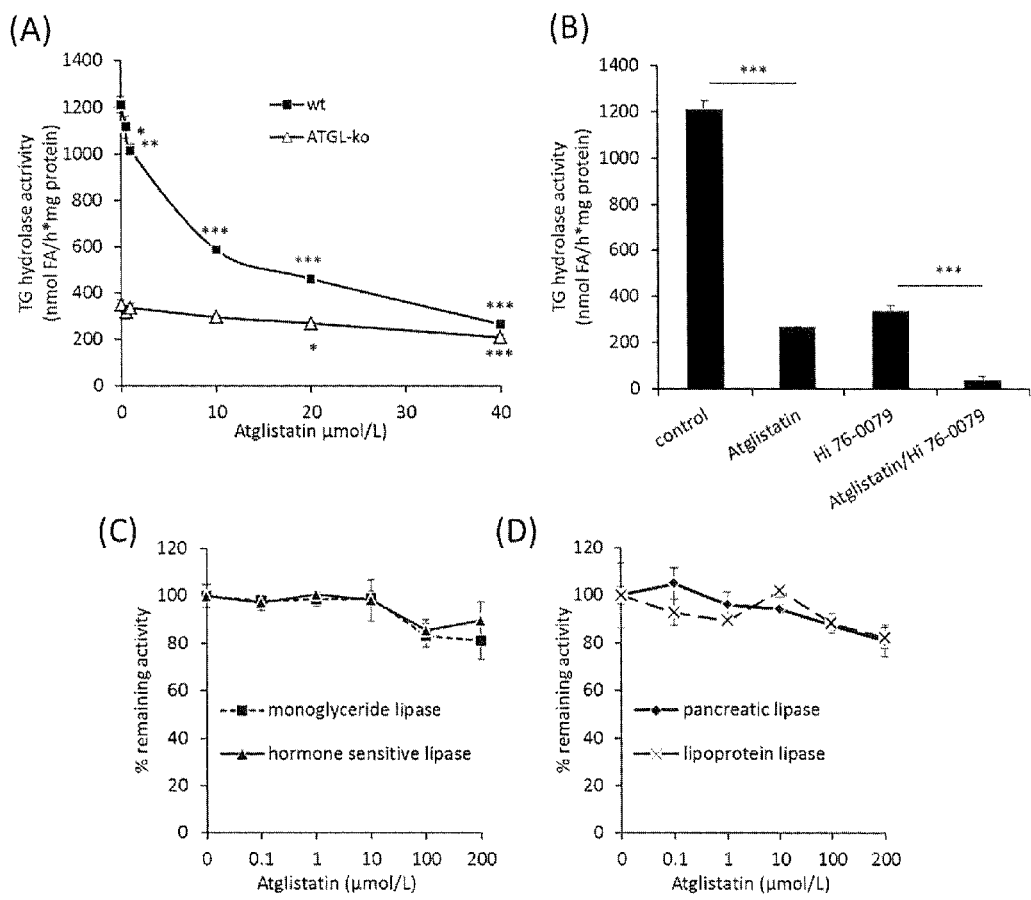
FIGS. 2(A), 2(B), 2(C) and 2(D) are graphs that illustrate the selectivity of Atglistatin.

Inhibition of ATGL Activity in Adipose Tissue Lysates and Selectivity of Atglistatin To evaluate whether Atglistatin inhibits other lipases present in adipose tissue, white adipose tissue (WAT) lysates of wild-type and ATGL deficient mice were analysed for TG hydrolase activity in the presence and absence of Atglistatin. As shown in FIG. 2, Atglistatin inhibited TG hydrolase activity of wild-type WAT in a dose dependent manner (FIG. 2A) up to 78% at a concentration of 40 µM. Compared to the wild-type control, TG hydrolase activity in lysates obtained from ATGL-ko animals was reduced by approximately 70%. Notably, a moderate but significant effect of Atglistatin on the residual activity in these lysates was observed at concentrations ≥20 µM. This could indicate that Atglistatin inhibits other minor lipases that are structurally related to ATGL such as adiponutrin (PNPLA3). However, most of the remaining activity present in ATGL-ko lysates can be ascribed to HSL. As shown in FIG. 2B, the HSL inhibitor Hi 76-0079 decreased TG hydrolase activity in wild-type lysates by 72% which is primarily caused by defective DG degradation (Schweiger, 2006). In accordance with previous data (Schweiger, 2006), the combined use of Hi 76-0079 and Atglistatin led to an almost complete depletion of TG hydrolase activity (FIG. 2B).

Next, the effect of the inhibitor on various other intracellular and secreted lipases was determined. Atglistatin had only minor effects on HSL and MGL activity (FIG. 2C), the downstream lipases of ATGL, as well as on pancreatic lipase and lipoprotein lipase representing major secreted TG lipases in intestine and plasma, respectively (FIG. 2D). Together, these observations suggest that Atglistatin exhibits high selectivity for ATGL and does not interfere with other known secreted or intracellular acylglycerol lipases.

Example 5

Figure 3:
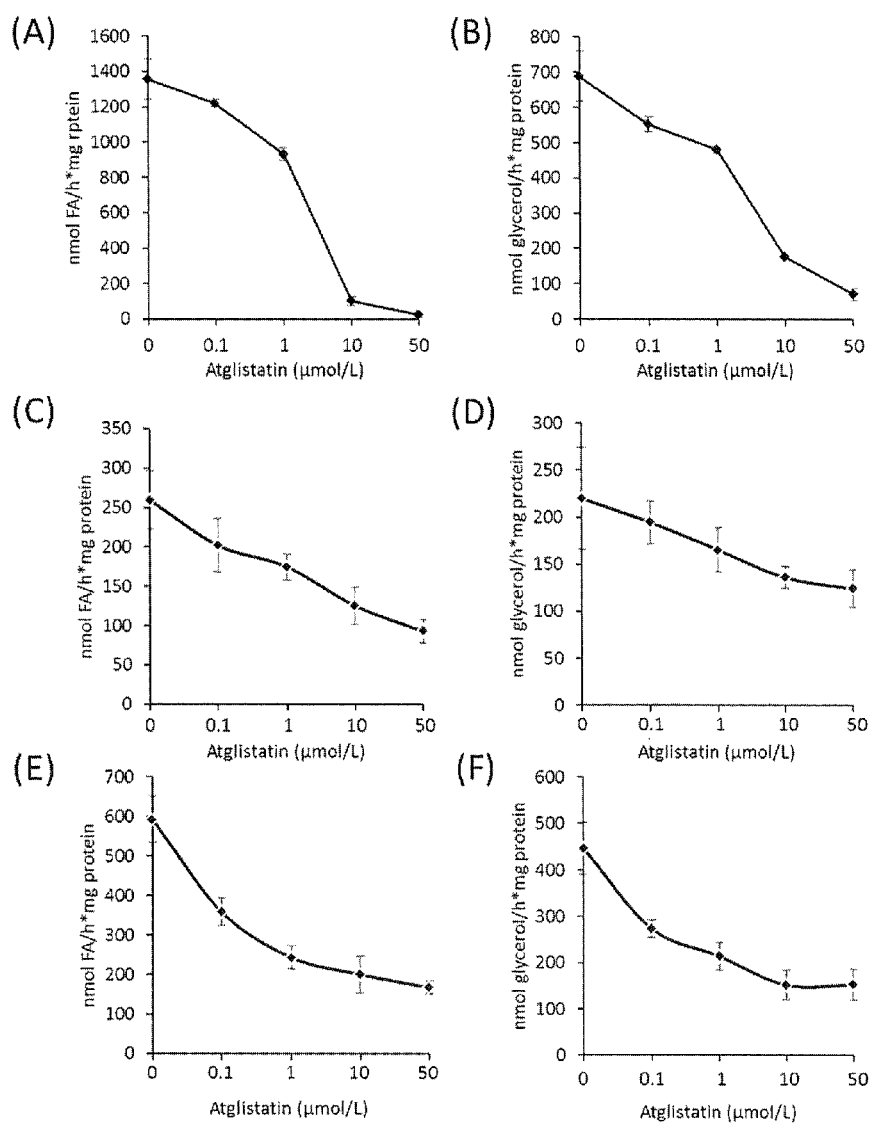
FIGS. 3(A) and 3(B) are graphs that illustrate the inhibition of lipolysis in 3T3-L1 adipocytes and WAT organ cultures by Atglisatin.
FIGS. 3(C) and 3(D) are graphs that illustrate show the effect of Atglistatin on WAT basal lipolysis.
FIGS. 3(E) and 3(F) are graphs that illustrate show the effect of Atglistatin on forskolin-stimulated lipolysis.

Inhibition of Lipolysis in 3T3-L1 Adipocytes and Organ Cultures of Murine White Adipose Tissue To test the effect of Atglistatin on cellular lipolysis, differentiated 3T3-L1 adipocytes were preincubated for 4 hours in the presence or in the absence of the inhibitor and subsequently stimulated with forskolin to induce lipolysis. Atglistatin reduced forskolin-stimulated lipolysis in a dose dependent manner resulting in almost complete inhibition of FA release (FIG. 3A) and ~90% inhibition of glycerol release (FIG. 3B). The inhibitor was also highly effective in WAT organ cultures of wild-type mice. Incubation of WAT organ cultures for 8 h reduced basal lipolysis (FIG. 3 C, D) and hormone-stimulated lipolysis in a dose dependent manner (FIG. 3 E, F). Under the applied conditions, forskolin-stimulated FA and glycerol release were reduced up to 72% and 66%, respectively. These results demonstrate that Atglistatin is able to inhibit lipolysis on the cellular and organ level.

Example 6

Inhibition of Lipolysis in vivo

The in vivo effect of Atglistatin on lipolysis was tested in fasted wild-type C57Bl/6J mice. Fasted animals received an oral gavage of olive oil containing the inhibitor or olive oil alone. Before gavage, as well as 4 h, 8 h, 12 h, and 16 h after gavage blood was collected by retro-orbital puncture and plasma FA and glycerol concentrations were determined. Atglistatin lead to a time dependent decrease in plasma levels for FA and for glycerol between 4 h and 12 h, and between 4 h and 8 h after gavage, respectively (FIG. 4A,B). Moreover, Atglistatin produced a dose-dependent decrease in plasma FA and glycerol levels up to 50% and 70%, respectively (FIG. 4C,D).

Detailed analyses of plasma parameters revealed that the Atglistatin group exhibited significantly reduced plasma FA, glycerol, and TG levels. Plasma glucose, total cholesterol, and insulin levels remained unchanged (Table 1A).

ATGL-deficiency in mice has been shown to cause TG accumulation in many tissues which is most pronounced in the heart. Importantly, Atglistatin did not promote the accumulation of TG in cardiac muscle and other tissues including skeletal muscle, adipose tissue, testis, pancreas, liver, and kidney (Table 1B).

TALE 1

Inhibition of lipolysis in vivo. C57Bl6 mice were fasted overnight and received an oral gavage containing 200 μmol/kg Atglistatin dissolved in olive oil, or olive oil as control. After 8 h blood was taken retroorbitally and mice were sacrificed. (A) Plasma parameters were measured using commercial kits. (B) Tissue triglyceride (TG) and protein levels were determined in whole tissue lysates and are presented as TG (nmol) per protein (mg).

(A)

|  | Control | Atglistatin |
|---|---|---|
| FFA (mmol/L) | 0.77 ± 0.13 | 0.53 ± 0.05 *** |
| Glycerol (mmol/L) | 0.41 ± 0.05 | 0.31 ± 0.08* |
| Triglycerides (mmol/L) | 0.58 ± 0.08 | 0.33 ± 0.14** |
| Glucose (mg/dL) | 78.85 ± 7.99 | 86.85 ± 12.19 |
| CE (mmol/L) | 3.25 ± 0.44 | 3.12 ± 0.25 |
| Insulin (ng/ml) | 0.17 ± 0.06 | 0.18 ± 0.07 |

(B)

|  | Control (nmol TG/mg protein) | Atglistatin (nmol TG/mg protein) |
|---|---|---|
| skeletal muscle | 74 ± 17 | 99 ± 13 |
| cardiac muscle | 76 ± 17 | 71 ± 19 |
| adipose tissue | 6092 ± 630 | 6218 ± 742 |
| testis | 146 ± 50 | 168 ± 36 |
| pancreas | 115 ± 32 | 131 ± 39 |
| liver | 132 ± 30 | 112 ± 14 |
| kidney | 84 ± 16 | 72 ± 15 |

Data are presented as mean + S.D.
(*p < 0.05
**p < 0.01;
*** p < 0.001).
n = 7

Example 7

Screening

Lipase Assay (Triacylgycerol Hydrolase Assay):

Mesenteric, retroperitoneal, omental and, gonadal white adipose tissues (WAT) of mice were removed surgically and, washed in phosphate-buffered saline (PBS) containing 1 mM ethylenediaminetetraacetic-acid(EDTA). The tissue was homogenized in lysis buffer (0.25 M sucrose, 1 mM EDTA, 1 mM dithiothreitol, 20 μg/ml leupeptin, 2 μg/ml antipain, 1 μg/ml pepstatin, pH 7.0) using a Magna Lyser (Roche diagnostics GmbH, Mannheim, Germany). The WAT lysate was centrifuged at 100,000 g for 1 hour (h) at 4° C. The lipid-free infranatant (cytosolic fraction) was collected and, used for triacyl-glycerol (TG) hydrolase assays. The substrate for the measurement of lipase activity containing triolein and [9,10-3H(N)-triolein] (NEN Life Science Products, Boston, Mass.) as radioactive tracer was emulsified with phosphatidylcholine/phosphatidylinositol using a conventional ultrasound sonicator. The cytosolic fractions supplemented with or, without a specific inhibitor for HSL were incubated at 37° C. for 60 min under constant shaking. The reaction was terminated by addition of 3.25 ml methanol/chloroform/heptane (10:9:7) and, 1 ml of 0.1 M potassium carbonate and, 0.1 M boric acid (pH 10.5). After centrifugation at 800 g for 20 minutes(min) the radioactivity in 1 ml of the upper phase was determined by liquid scintillation counting in a LS 6500 Multi-Purpose Scintillation Counter from Beckman Coulter Inc. (Fullerton, Calif.). The activity of ATGL can primarily be measured by cleavage of triglycerides (exemplary assay provided directly above or in example 1 above; Lipase Assay), because the enzyme does not recognize water-soluble substrates. Using this method, about 300 measurements can be carried out per day by one person in a high throughput assay.

ATGL activity may also be measured using cell culture. Preadipocyte-lines, e.g. 3T3-L1 cells, are differentiated to adipocytes. Then after beta-adrenergic stimulation, these cells secrete large amounts of glycerol and fatty acids into the culture medium, which can be measured easily using commercial enzymatic kits. By incubation with inhibitors, this secretion can be inhibited. In the absence of ATGL, the secretion is inhibited by about 70%. In the absence of HSL and ATGL, there is almost no beta-adrenergic stimulation of lipolysis in adipocytes (Schweiger M et al (2006) J Biol Chem 281(52):40236-40241). Therefore, in the presence of an HSL inhibitor (such as 76-0079, Novo Nordisk), specific ATGL activity can be determined in living adipocytes (Schweiger M et al (2006) J Biol Chem 281(52):40236-40241).

ATGL inhibitory activity of a phospholipase-inhibitor (R)-Bromoenol lactone (Cayman Chemicals, Cat. No. 10006800, CAS No. 478288-90-3) has been demonstrated with expressed ATGL (Jenkins C M et al (2004) J Biol Chem 279(47):48968-48975) or native ATGL in hepatocytes (Chung C et al (2008) J Hepatol 48:471-41-478). This lipase inhibitor also inhibits other lipases including iPLA2β and iPLA2γ (Mancuso D J et al (2000) J boil Chem 275:9937-9945; Hazen S et al (1991) J Biol Chem 266:7227-7232; Zupan L A et al (1993) J med Chem 36:95-100). This provides an ATGL inhibiting compound for studies, assessment, and as a control in further screening.

To further assess ATGL hydrolysis of neutral lipids, His-tagged ATGL can be transiently expressed in COS-7 cells using a eukaryotic expression vector. For comparison, COS-7 cells are also transfected with a similar construction expressing His-tagged HSL. In an alternative embodiment, strep-tagged ATGL and CGI-58 are expressed in E. coli. Extracts from transfected cells are preincubated with an inhibitor or candidate compound or compound library. When extracts are preincubated with the fluorescent lipase inhibitor (NBD-HEHP) and subsequently subjected to SDS-PAGE analysis and fluorography, fluorescent signals can be observed in positions corresponding to the expected molecular weight of ATGL and HSL providing evidence that ATGL is enzymatically active in transfected COS cells. To confirm ATGL activity, TG-hydrolase activity assays can be performed using a radioactively labelled [9,10-3H(N))]-triolein substrate. As controls, no enzymatic activities should be observed when radioactively labeled retinyl palmitate, cholesteryl oleate or phosphatidylcholine are used as lipid substrates.

To determine ATGL function in adipocytes, including in assays in the presence or absence of one or more candidate compounds, modulators, or inhibitors, a recombinant adenovirus encoding His-tagged full length mouse or human ATGL cDNA is constructed and used to infect mouse 3T3-L1 adipocytes at day 6 of differentiation. Western blotting analysis of cell-extracts of infected adipocytes reveals expression of His-tagged ATGL at the appropriate molecular weight. Overexpression of ATGL in adipocytes can markedly augment both basal and isoproterenol-stimulated lipolysis, indicative of a functional ATGL lipase in adipose tissue.

References

1. Lass, A., Zimmermann, R., Oberer, M. & Zechner, R. Lipolysis—a highly regulated multi-enzyme complex mediates the catabolism of cellular fat stores. Prog Lipid Res 50, 14-27.
2. Zimmermann, R. et al. Fat mobilization in adipose tissue is promoted by adipose triglyceride lipase. Science 306, 1383-6 (2004).
3. Haemmerle, G. et al. Hormone-sensitive lipase deficiency in mice causes diglyceride accumulation in adipose tissue, muscle, and testis. J Biol Chem 277, 4806-15 (2002).
4. Fredrikson, G., Tornqvist, H. & Belfrage, P. Hormone-sensitive lipase and monoacylglycerol lipase are both required for complete degradation of adipocyte triacylglycerol. Biochim Biophys Acta 876, 288-93 (1986).
5. Lass, A. et al. Adipose triglyceride lipase-mediated lipolysis of cellular fat stores is activated by CGI-58 and defective in Chanarin-Dorfman Syndrome. Cell Metab 3, 309-19 (2006).
6. Lefevre, C. et al. Mutations in CGI-58, the gene encoding a new protein of the esterase/lipase/thioesterase subfamily, in Chanarin-Dorfman syndrome. Am J Hum Genet 69, 1002-12 (2001).
7. Fischer, J. et al. The gene encoding adipose triglyceride lipase (PNPLA2) is mutated in neutral lipid storage disease with myopathy. Nat Genet 39, 28-30 (2007).
8. Haemmerle, G. et al. Defective lipolysis and altered energy metabolism in mice lacking adipose triglyceride lipase. Science 312, 734-7 (2006).
9. Wu, J. W. et al. Fasting energy homeostasis in mice with adipose deficiency of desnutrin/adipose triglyceride lipase. Endocrinology 153, 2198-207 (2012).
10. Ahmadian, M. et al. Adipose overexpression of desnutrin promotes fatty acid use and attenuates diet-induced obesity. Diabetes 58, 855-66 (2009).
11. Boden, G. Obesity, insulin resistance and free fatty acids. Curr Opin Endocrinol Diabetes Obes 18, 139-43 (2011).
12. Carobbio, S., Rodriguez-Cuenca, S. & Vidal-Puig, A. Origins of metabolic complications in obesity: ectopic fat accumulation. The importance of the qualitative aspect of lipotoxicity. Curr Opin Clin Nutr Metab Care 14, 520-6 (2011).
13. Ebdrup, S., Sorensen, L. G., Olsen, O. H. & Jacobsen, P. Synthesis and structure-activity relationship for a novel class of potent and selective carbamoyl-triazole based inhibitors of hormone sensitive lipase. J Med Chem 47, 400-10 (2004).
14. Ebdrup, S., Refsgaard, H. H., Fledelius, C. & Jacobsen, P. Synthesis and structure-activity relationship for a novel class of potent and selective carbamate-based inhibitors of hormone selective lipase with acute in vivo antilipolytic effects. J Med Chem 50, 5449-56 (2007).
15. He, S. et al. A sequence variation (I148M) in PNPLA3 associated with nonalcoholic fatty liver disease disrupts triglyceride hydrolysis. J Biol Chem 285, 6706-15 (2010).
16. Schweiger, M. et al. Adipose triglyceride lipase and hormone-sensitive lipase are the major enzymes in adipose tissue triacylglycerol catabolism. J Biol Chem 281, 40236-41 (2006).
17. Kienesberger, P. C. et al. Adipose triglyceride lipase deficiency causes tissue-specific changes in insulin signaling. J Biol Chem 284, 30218-29 (2009).
18. Li, L. O., Klett, E. L. & Coleman, R. A. Acyl-CoA synthesis, lipid metabolism and lipotoxicity. Biochim Biophys Acta 1801, 246-51 (2010).
19. Summers, S. A. Ceramides in insulin resistance and lipotoxicity. Prog Lipid Res 45, 42-72 (2006).
20. Samuel, V. T., Petersen, K. F. & Shulman, G. I. Lipid-induced insulin resistance: unravelling the mechanism. Lancet 375, 2267-77 (2010).
21. Haemmerle, G. et al. ATGL-mediated fat catabolism regulates cardiac mitochondrial function via PPAR-alpha and PGC-1. Nat Med 17, 1076-85 (2011).
22. Hirano, K., Ikeda, Y., Zaima, N., Sakata, Y. & Matsumiya, G. Triglyceride deposit cardiomyovasculopathy. N Engl J Med 359, 2396-8 (2008).
23. Hirano, K. A novel clinical entity: triglyceride deposit cardiomyovasculopathy. J Atheroscler Thromb 16, 702-5 (2009).
24. Tisdale, M. J. Cancer cachexia. Curr Opin Gastroenterol 26, 146-51 (2010).
25. Ryden, M. et al. Lipolysis—not inflammation, cell death, or lipogenesis—is involved in adipose tissue loss in cancer cachexia. Cancer 113, 1695-704 (2008).
26. Deans, C. & Wigmore, S. J. Systemic inflammation, cachexia and prognosis in patients with cancer. Curr Opin Clin Nutr Metab Care 8, 265-9 (2005).
27. Das, S. K. et al. Adipose triglyceride lipase contributes to cancer-associated cachexia. Science 333, 233-8.
28. Honors, M. A. & Kinzig, K. P. The role of insulin resistance in the development of muscle wasting during cancer cachexia. J Cachexia Sarcopenia Muscle 3, 5-11 (2012).
29. Tamilarasan, K. P. et al. Skeletal muscle damage and impaired regeneration due to LPL-mediated lipotoxicity. Cell Death Dis 3, e354 (2012).
30. Taschler, U. et al. Monoglyceride lipase deficiency in mice impairs lipolysis and attenuates diet-induced insulin resistance. J Biol Chem 286, 17467-77 (2011).
31. Busquets, S., Figueras, M. T., Fuster, G., Almendro, V., Moore-Carrasco, R., Ametller, E., Argiles, J. M., and Lopez-Soriano, F. J. (2004). Anticachectic effects of formoterol: a drug for potential treatment of muscle wasting. Cancer Res 64, 6725-6731.
32. Tinsley, F. C., Taicher, G. Z., and Heiman, M. L. (2004). Evaluation of a quantitative magnetic resonance method for mouse whole body composition analysis. Obes Res 12, 150-160.
33. Ventrucci, G., Mello, M. A., and Gomes-Marcondes, M. C. (2004). Proteasome activity is altered in skeletal muscle tissue of tumour-bearing rats a leucine-rich diet. Endocr Relat Cancer 11, 887-895.

What is claimed is:
1. A compound having the following formula:
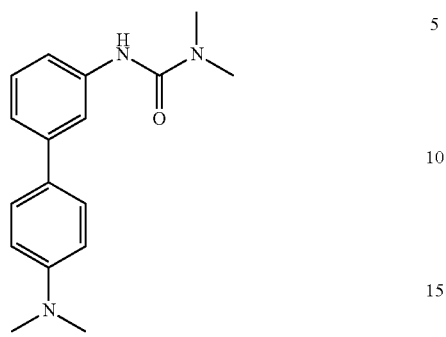
or a pharmaceutically acceptable salt or solvate thereof.
2. A pharmaceutical composition comprising the compound of claim 1 and a pharmaceutically acceptable excipient.
* * * * *